(12) United States Patent
Yang et al.

(10) Patent No.: US 12,064,759 B2
(45) Date of Patent: Aug. 20, 2024

(54) MICROFLUIDIC DEVICE WITH EMBEDDED CELL CULTURE CHAMBERS FOR HIGH THROUGHPUT BIOLOGICAL ASSAYS

(71) Applicants: NUtech Ventures, Lincoln, NE (US); UNIVERSITY OF CONNECTICUT, Farmington, CT (US)

(72) Inventors: Ruiguo Yang, Lincoln, NE (US); Arian Jaberi, Lincoln, NE (US); Amir Monemian Esfahani, Lincoln, NE (US); Ali Tamayol, Providence, RI (US)

(73) Assignees: NUTECH VENTURES, Lincoln, NE (US); UNIVERSITY OF CONNECTICUT, Farmington, CT (US)

( * ) Notice: Subject to any disclaimer, the term of this patent is extended or adjusted under 35 U.S.C. 154(b) by 257 days.

(21) Appl. No.: 17/245,381

(22) Filed: Apr. 30, 2021

(65) Prior Publication Data
US 2021/0339242 A1 Nov. 4, 2021

Related U.S. Application Data

(60) Provisional application No. 63/017,820, filed on Apr. 30, 2020.

(51) Int. Cl.
*B01L 3/00* (2006.01)
*C12M 1/34* (2006.01)
*C12N 1/34* (2006.01)

(52) U.S. Cl.
CPC .......... *B01L 3/5025* (2013.01); *C12M 41/46* (2013.01); *C12N 1/34* (2013.01); *B01L 2300/087* (2013.01);
(Continued)

(58) Field of Classification Search
None
See application file for complete search history.

(56) References Cited

U.S. PATENT DOCUMENTS

2005/0217750 A1* 10/2005 Jeon ...................... B01F 25/432
141/9
2011/0269226 A1* 11/2011 Van Noort ............. C12M 29/10
435/325
(Continued)

FOREIGN PATENT DOCUMENTS

| CN | 101629143 A | 1/2010 | |
|---|---|---|---|
| CN | 106497771 A | 3/2017 | |
| WO | WO0188525 A1 * | 11/2001 | ............. G01N 27/26 |

OTHER PUBLICATIONS

Zhang et al., Advances in Organ-on-a-Chip Engineering, Nature Reviews Materials, 2018, 3(8):257-278.
(Continued)

*Primary Examiner* — Lore R Jarrett
(74) *Attorney, Agent, or Firm* — Quarles & Brady LLP

(57) ABSTRACT

Microfluidic gradient generators that can create robust platforms that can not only be used for creating co-cultures of cells with various ratios, but also can simultaneously generate gradients of mechanical and chemical stresses. A chip utilizes microchambers embedded within channels to provide space for 3D cell culture and exposes these cells to gradients of mechanical shear stress and a chemical treatment.

17 Claims, 13 Drawing Sheets
(13 of 13 Drawing Sheet(s) Filed in Color)

(52) U.S. Cl.
CPC ............... *B01L 2300/0877* (2013.01); *B01L 2300/0883* (2013.01); *C12N 2513/00* (2013.01)

(56) References Cited

U.S. PATENT DOCUMENTS

| | | | | |
|---|---|---|---|---|
| 2012/0003732 | A1* | 1/2012 | Hung | C12M 23/34 435/289.1 |
| 2017/0067009 | A1* | 3/2017 | Sloane | C12M 23/22 |
| 2018/0127699 | A1* | 5/2018 | Li | B01L 3/502761 |
| 2018/0280976 | A1* | 10/2018 | Lelièvre | B01F 25/4331 |
| 2019/0009274 | A1* | 1/2019 | Novak | G01N 33/5088 |
| 2019/0161736 | A1* | 5/2019 | Khoo | A61B 5/151 |
| 2020/0038861 | A1* | 2/2020 | Yoon | C12M 41/46 |

OTHER PUBLICATIONS

Zhao et al., Simultaneous Orientation and Cellular Force Measurements in Adult Cardiac Myocytes Using Three-Dimensional Polymeric Microstructures, Cell Motility and the Cytoskeleton, 2007, 64(9):718-725.

Zheng et al., In Vitro Microvessels for the Study of Angiogenesis and Thrombosis, Proceedings of the National Academy of Sciences, 2012, 109(24):9342-9347.

Anand et al., Application of a Fluorescence Resonance Energy Transfer (FRET)-Based Biosensor for Detection of Drug-Induced Apoptosis in a 3D Breast Tumor Model, Biotechnology and Bioengineering, 2015, 112(8):1673-1682.

Baker, A Living System on a Chip, Nature, 2011, 471(7340):661-665.

Bhise et al., A Liver-on-a-Chip Platform with Bioprinted Hepatic Spheroids, Biofabrication, 2016, 8(1):014101, pp. 1-12.

Caliari et al., A Practical Guide to Hydrogels for Cell Culture, Nature Methods, 2016, 13(5):405-414.

Castiaux et al., Review of 3D Cell Culture with Analysis in Microfluidic Systems, Analytical Methods, 2019, 11(33):4220-4232.

Chan et al., Accelerating Drug Discovery via Organs-on-Chips, Lab on a Chip, 2013, 13(24):4697-4710.

Chatterjee et al., Doxorubicin Cardiomyopathy, Cardiology, 2010, 115(2):155-162.

Chen et al., Insert-Based Microfluidics for 3D Cell Culture with Analysis, Analytical and Bioanalytical Chemistry, 2018, 410(12):3025-3035.

Duval et al., Modeling Physiological Events in 2D vs. 3D Cell Culture, Physiology, 2017, 32(4):266-277.

Englert et al., Flow-Based Microfluidic Device for Quantifying Bacterial Chemotaxis in Stable, Competing Gradients, Applied and Environmental Microbiology, 20009, 75(13):4557-4564.

Frey et al., Reconfigurable Microfluidic Hanging Drop Network for Multi-Tissue Interaction and Analysis, Nature Communications, 2014, 5:4250, pp. 1-11.

Gao et al., Evaluation of the Absorption of Methotrexate on Cells and its Cytotoxicity Assay by Using an Integrated Microfluidic Device Coupled to a Mass Spectrometer, Analytical Chemistry, 2012, 84(21):9230-9237.

Germain et al., Observation of Reversible, Rapid Changes in Drug Susceptibility of Hypoxic Tumor Cells in a Microfluidic Device, Analytica Chimica Acta, 2016, 936:179-184.

Ghorbanian et al., Direct Writer with Integrated Declogging Mechanism for Fabricating Cell-Laden Hydrogel Constructs, Biomedical Microdevices, 2014, 16(3):387-395.

Guo et al., Neuromuscular Junction Formation Between Human Stem Cell-Derived Motoneurons and Human Skeletal Muscle in a Defined System, Biomaterials, 2011, 32(36):9602-9611.

Han et al., Chemoresistance in the Human Triple-Negative Breast cancer Cell Line MDA-MB-231 Induced by Doxorubicin Gradient is Associated with Epigenetic Alterations in Histone Deacetylase, Journal of Oncology, 2019, vol. 2019, Article ID 1345026, 12 pages.

Huh et al., Reconstituting Organ-Level Lung Functions on a Chip, Science, 2010, 328(5986):1662-1668.

Ivich et al., Application of a Microfluidic-Based Model of a Human Prostate Gland for Cancer Research, In 2018 IEEE 12th International Conference on Nano/Molecular Medicine and Engineering (NANOMED), pp. 109-112.

Jang et al., Human Kidney Proximal Tubule-on-a-Chip for Drug Transport and Nephrotoxicity Assessment, Integrative Biology, 2013, 5(9):1119-1129.

Jeon et al., Neutrophil Chemotaxis in Linear and Complex Gradients of Interleukin-8 Formed in a Microfabricated Device, Nature Biotechnology, 2002, 20(8):826-830.

Jie et al., Integrated Microfluidic System for Cell Co-Culture and Simulation of Drug Metabolism, RSC Advances, 2016, 6(59):54564-54572.

Kang et al., Digitally Tunable Physicochemical Coding of Material Composition and Topography in Continuous Microfibres, Nature Materials, 2011, 10(11):877-883.

Khetani et al., Microscale Culture of Human Liver Cells for Drug Development, Nature Biotechnology, 2008, 26(1):120-126.

Kim et al., Biological Applications of Microfluidic Gradient Devices, Integrative Biology, 2010, 2(11-12):584-603.

Kim et al., Human Gut-on-a-Chip Inhabited by Microbial Flora that Experiences Intestinal Peristalsis-Like Motions and Flow, Lab on a Chip, 2012, 12(12):2165-2174.

Lee et al., Dynamic Cell Culture: A Microfluidic Function Generator for Live Cell Microscopy, Lab on a Chip, 2009, 9(1):164-166.

Lee et al., Fluid Shear Stress Activates YAP1 to Promote Cancer Cell Motility, Nature Communications, 2017, 8(1):1-14.

Linder et al., Application of Surface Biopassivated Disposable Poly (Dimethylsiloxane)/Glass Chips to a Heterogeneous Competitive Human Serum Immunoglobulin G Immunoassay with Incorporated Internal Standard, Electrophoresis, 2002, 23(5):740-749.

Park et al., Differentiation of Neural Progenitor Cells in a Microfluidic Chip-Generated Cytokine Gradient, Stem Cells, 2009, 27(11):2646-2654.

Polacheck et al., Mechanotransduction of Fluid Stresses Governs 3D Cell Migration, Proceedings of the National Academy of Sciences, 2014, 111(7):2447-2452.

Regmi et al., High Shear Stresses Under Exercise Condition Destroy Circulating Tumor Cells in a Microfluidic System, Scientific Reports, 2017, 7(1):1-12.

Rezaei Nejad et al., Laterally Confined Microfluidic Patterning of Cells for Engineering Spatially Defined Vascularization, Small, 2016, 12(37):5132-5139.

Rizvi et al., Flow Induces Epithelial-Mesenchymal Transition, Cellular Heterogeneity and Biomarker Modulation in 3D Ovarian Cancer Nodules, Proceedings of the National Academy of Sciences, 2013, 110(22):E1974-E1983.

Ruiz et al., Testing AB Toxicity on Primary CNS Cultures Using Drug-Screening Microfluidic Chips, Lab on a Chip, 2014, 14(15):2860-2866.

Shamloo et al., Endothelial Cell Polarization and Chemotaxis in a Microfluidic Device, Lab on a Chip, 2008, 8(8):1292-1299.

Shang et al., Microfluidic Modelling of the Tumor Microenvironment for Anti-Cancer Drug Development, Lab on a Chip, 2019, 19(3):369-386.

Shemesh et al., Flow-Induced Stress on Adherent Cells in Microfluidic Devices, Lab on a Chip, 2015, 15(21):4114-4127.

Sugiura et al., Microfluidic Serial Dilution Cell-Based Assay for Analyzing Drug Dose Response Over a Wide Concentration Range, Analytical Chemistry, 2010, 82(19):8278-8282.

Sung et al., Recent Advances in Body-on-a-Chip Systems, Analytical Chemistry, 2018, 91(1):330-351.

Tamayol et al., Hydrogel Templates for Rapid Manufacturing of Bioactive Fibers and 3D Constructs, Advanced Healthcare Materials, 2015, 4(14):2146-2153.

Triantafillu et al., Fluid Shear Stress Induces Drug Resistance to Doxorubicin and Paclitaxel in the Breast Cancer Cell Line MCF7, Advanced Therapeutics, 2019, 2(3):1800112.

(56) References Cited

OTHER PUBLICATIONS

Wallin et al., A Method to Integrate Patterned Electrospun Fibers with Microfluidic Systems to Generate Complex Microenvironments for Cell Culture Applications, Biomicrofluidics, 2012, 6(2):024131.

Wang et al., Differential Effects of EGF Gradient Profiles on MDA-MB-231 Breast Cancer Cell Chemotaxis, Experimental Cell Research, 2004, 300(1):180-189.

Wang et al., A Rapid Pathway Toward a Superb Gene Delivery System: Programming Structural and Functional Diversity into a Supramolecular Nanoparticle Library, ACS Nano, 2010, 4(10):6235-6243.

Wolfram et al., Perspectives in Flow-Based Microfluidic Gradient Generators for Characterizing Bacterial Chemotaxis, Biomicrofluidics, 2016, 10(6):061301, pp. 1-12.

Xiong et al., Involvement of Caveolin-1 in Low Shear Stress-Induced Breast Cancer Cell Motility and Adhesion: Roles of FAK/Src and ROCK/p-MLC Pathways, Biochimica et Biophysica Acta (BBA)—Molecular Cell Research, 2017, 1864(1):12-22.

Yankaskas et al., A Microfluidic Assay for the Quantification of the Metastatic Propensity of Breast Cancer Specimens, Nature Biomedical Engineering, 2019, 3(6):452-465.

Yuan et al., Co-Culture of Tumor Spheroids and Monocytes in a Collagen Matrix-Embedded Microfluidic Device to Study the Migration of Breast Cancer Cells, Chinese Chemical Letters, 2019, 30(2):331-336.

Yue et al., Synthesis, Properties, and Biomedical Applications of Gelatin Methacryloyl (GelMA) Hydrogels, Biomaterials, 2015, 73:254-271.

Zaidon et al., Serpentine Microfluidic Structures for Concentration Gradient Generators, In 2016 Symposium on Design, Test, Integration and Packaging of MEMS/MOEMS (DTIP), IEEE, 2016, pp. 1-5.

\* cited by examiner

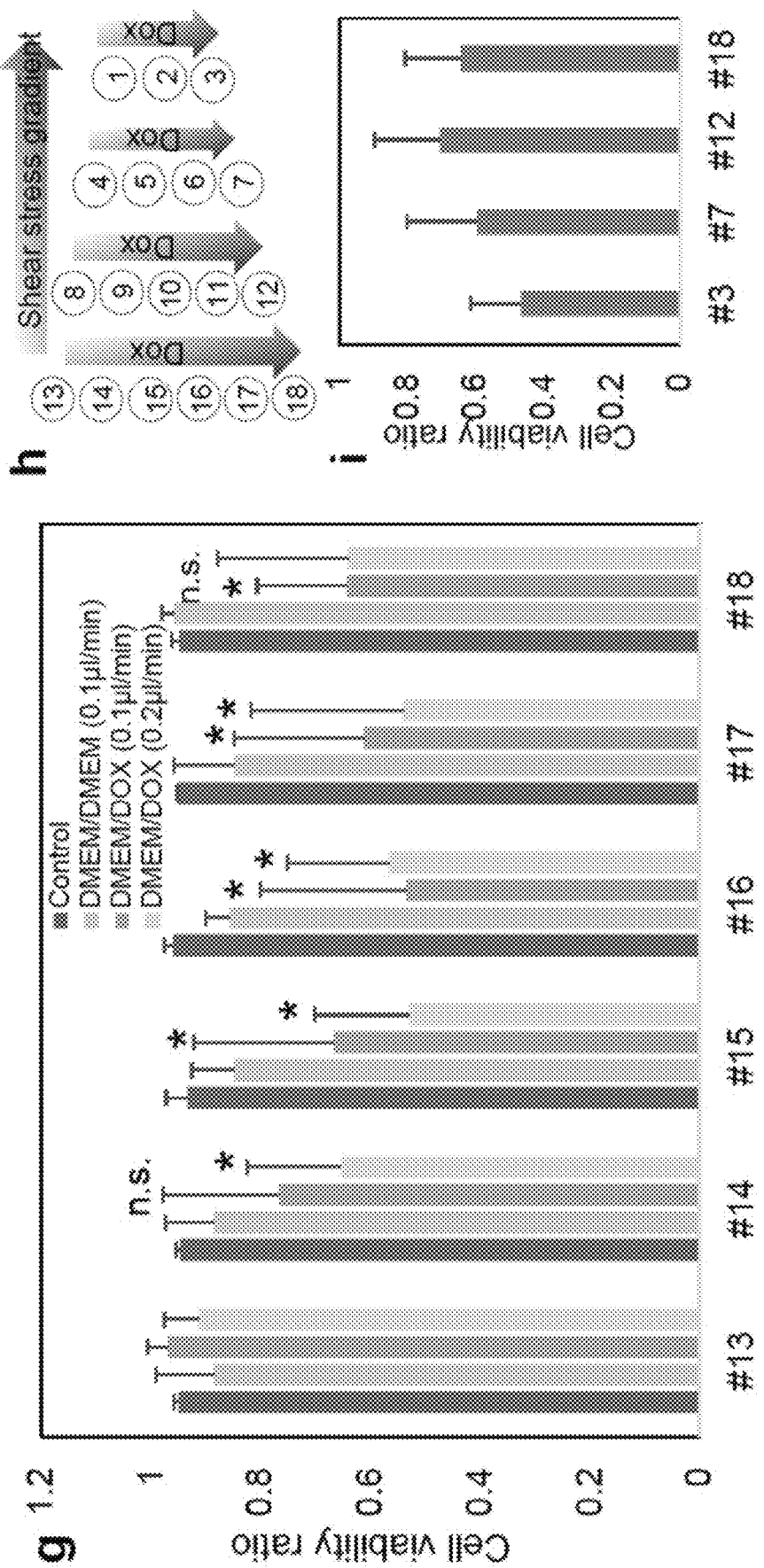
FIG. 6 (con't.)

MICROFLUIDIC DEVICE WITH EMBEDDED CELL CULTURE CHAMBERS FOR HIGH THROUGHPUT BIOLOGICAL ASSAYS

CROSS-REFERENCE TO RELATED APPLICATIONS

The present application is based on and claims priority from U.S. Patent Application Ser. No. 63/017,820, filed on Apr. 30, 2020, the entire disclosure of which is incorporated herein by reference.

GOVERNMENT SUPPORT STATEMENT

This invention was made with government support under 1826135 awarded by the National Science Foundation and under P20 GM113126 and P30 GM127200 awarded by the National Institutes of Health. The government has certain rights in the invention.

BACKGROUND

Organs-on-a-chip platforms are emerging tools combining the advancements in microfluidics, biomaterials, and biofabrication aimed at complementing conventional in vitro assays and animal models. However, known platforms have deficiencies that make them unsatisfactory for certain assays.

SUMMARY OF THE PRESENT DISCLOSURE

Thus, improved platforms for generating chemical and mechanical gradients on chips are needed and such platforms are important both for creating biomimetic designs or enabling high throughput assays on a single chip. However, there is still significant knowledge gap in the generation of mechanical and chemical gradient in a single device.

The continued advancement in microfluidic technology has enabled the creation of cellular microenvironments that mimic the physiology of tissues and organs in the human body. The so-called organ-on-a-chip micro-devices enable the interaction of heterogeneous cells for a collective response, similar to the interactions in vivo in the functional units of the body. Over the years, devices mimicking the functional units of the liver, the lung, muscles, the kidney, the microvascular networks, and so on, have been proposed and tested. In the short time span, these platforms have demonstrated the potential for high throughput drug discovery and toxicity screening, filling the gap between in vitro drug tests and animal models. For drug screening and toxicity tests, however, two important component of the organ-on-a-chip devices must be considered: the on-device cell culture and the profusion based chemical gradient generation.

In newly developed microfluidic devices, the traditional 2D cell culture practices have given way to 3D cell culture schemes to closely recapitulate the microenvironment in vivo. 3D cell culture platforms allow for omnidirectional cellular growth with biomimetic cell-cell and cell-extracellular matrix (ECM) interactions. 3D cell culture using hydrogels, fibrous scaffolds, and droplet suspensions within microfluidic devices has demonstrated different drug responses, cell morphologies, and proliferation patterns than static 2D cell cultures. Microfluidic systems have also been utilized for creating cellular patterns in 2D and 3D environments. These devices have shown a great promise for depositing cells in a highly defined fashion and over a scale of several centimeters. Despite these progresses, the capability of such systems for engineering co-culture of different cells is not well-explored, especially considering the potential of co-cultures exposed to different drug compounds.

The length scale of the microfluidic devices and the availability of many user-defined designs combined with the microfluidic handling capabilities make them ideal platforms for drug screening. In fact, the generation of spatial and temporal chemical gradients in microfluidic devices have been widely reported to study the efficacy and toxicity of drugs and examine their effects on cellular behaviors, such as cancer metastasis, angiogenesis and stem cell differentiation. In addition, the versatile gradient generation methods for chemokines also provide a convenient solution for various immunoassays. Microfluidic devices have also emerged as a robust tool for applying mechanical cues to cell cultures. These cues can significantly affect the function and viability of cells. For instance, in the study of cancer cells' response to epidermal growth factor (EGF), it has been shown that breast cancer cells respond to mechanical stimuli more evidently than chemical gradients. Particularly, the effects of mechanical cues have been reported to exhibit in the form of increased cell mortality and decreased cell adhesion due to increased shear stress. These effects have been shown in prostate cancer cells, breast cancer cells, and epithelial ovarian cancer cells. In addition, the effect of the shear stress on inducing drug resistance on breast cancer cells has also been demonstrated. Thus, it is highly desirable to develop microfluidic chips that can effectively examine the effect of mechanical and chemical stimuli in one single platform. However, so far, no robust platform for studying the combined role of chemical and mechanical stimuli on the culture cells has been reported.

The present disclosure provides microfluidic gradient generators that can create robust platforms that can be used not only for creating co-cultures of cells with various ratios, but also can simultaneously generate gradients of mechanical and chemical stresses. This chip utilizes microchambers embedded within channels to provide space for 3D cell culture and exposes these cells to gradients of mechanical shear stress and chemical treatments. In various embodiments, the efficacy of an anti-cancer reagent in cancer cells in a dosage dependent fashion within the microchambers of the device may be demonstrated. Such results may be further confirmed in viability studies in standard dishes. Thus, embodiments of the disclosed platform will pave the way for drug screenings with different stimuli in a controlled 3D microenvironment.

In one embodiment, gradient generating microfluidic circuits with integrated microchambers which allow 3D cell culture and which allow the introduction of chemical and mechanical gradients to cultured cells are provided. In various embodiments, serpentine microchannels may be included produce chemical gradients; microchambers may be placed after each serpentine outlet to seed cells in a 3D environment. Chemical gradients may be generated across microchambers, while cells within each microchamber may receive a uniform concentration of drugs. To introduce gradients within a microchamber, micropillars may be placed within the chamber. Embodiments of the embedded microchamber not only enable screening of cellular responses to different concentrations of chemical compounds, but may also produce mechanical gradients in the form of different shear stresses induced upon cells among different chambers and within the same chamber.

In various embodiments, the gradient generation and cell seeding of both chips may be tested by comparing computational and experimental results. Cells seeded within the chambers remain viable and show normal morphology throughout the culture time. To validate the effect of different drug concentrations and shear stresses, doxorubicin can be flowed into the chambers seeded with skin cancer cells at different flow rate. Results show that increasing doxorubicin concentrations within chambers not only prohibit cell growth, but also induces cell death. In addition, the increased shear stress at high flow rate pose a synergistic effect on cell viability by inducing cell detachment and damage. One embodiment demonstrates the potential of microchamber embedded gradient generation in 3D cell culture and high throughput drug screening.

In one embodiment, a microfluidic gradient generator apparatus, including: a substrate including a plurality of microchannels and a plurality of microchambers formed therein, each of the plurality of microchambers including a first end and a second end and configured to permit fluid to flow from the first end to the second end, at least one of the first end or the second end of each of the plurality of microchambers being coupled to at least one of the plurality of microchannels, each of the plurality of microchannels and each of the plurality of microchambers being fluidly coupled to an inlet and an outlet such that fluid containing a material that is introduced at the inlet flows through at least one of the plurality of microchannels and at least one of the plurality of microchambers to the outlet, the plurality of microchannels and the plurality of microchambers on the substrate being configured so as to form a gradient of the material within the fluid.

In another embodiment, a method for generating a microfluidic gradient, including: providing a substrate including a plurality of microchannels and a plurality of microchambers formed therein, each of the plurality of microchambers including a first end and a second end and configured to permit fluid to flow from the first end to the second end, at least one of the first end or the second end of each of the plurality of microchambers being coupled to at least one of the plurality of microchannels, and each of the plurality of microchannels and each of the plurality of microchambers being fluidly coupled to an inlet and an outlet; introducing a fluid containing a material at the inlet such that the fluid flows through at least one of the plurality of microchannels and at least one of the plurality of microchambers to the outlet; and forming a gradient of the material within the fluid within the plurality of microchannels and the plurality of microchambers on the substrate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings are provided to help illustrate various features of example embodiments of the disclosure, and are not intended to limit the scope of the disclosure or exclude alternative implementations.

FIG. 1 panel (b) is a scanning electron microscope image of the MECT design of FIG. 1 panel (a).

FIG. 1 panel (c) is a COMSOL simulation design of a microchamber embedded microfluidic device for gradient generation and drug screening that includes micropillars built within the microchambers, the configuration referred to as MicroPillar Embedded Microchambers (MPEM).

FIG. 1 panel (d) is a scanning electron microscope image of the MPEM design of FIG. 1 panel (c).

FIG. 2b shows graphical comparisons of experimental data and simulation data of the simulations and tests of FIG. 2a.

FIG. 4b is a zoomed in fluorescent image of chamber #10 of FIG. 4a.

FIG. 4c is a zoomed in fluorescent image of chamber #11 of FIG. 4a.

FIG. 4d is a graphical cell ratio analysis of the third column of the chambers of FIG. 4a.

FIG. 4e is a graphical cell ratio analysis of the fourth column of the chambers of FIG. 4a.

FIG. 5 panel (b) is a shear stress distribution of a microchip at a flowrate of 0.1 µl/min at a 15 µm distance from a surface that shows the same trend of FIG. 5 panel (a).

FIG. 5 panel (c) is a shear stress distribution inside a chamber representative of chamber #2 of FIG. 5 panel (b).

FIG. 5 panel (d) is a velocity magnitude diagram of a microchip at a flow rate of 0.2 µl/min.

FIG. 5 panel (e) is a shear stress distribution of a microchip at a flowrate of 0.2 µl/min.

FIG. 5 panel (f) is a shear stress distribution along a symmetry line in chamber #2 of FIG. 5 panel (e).

FIG. 6 panel (b) is a fluorescent image of cells subject to 12 hours of flow of Dulbecco's Modified Eagle Medium (DMEM) from both inlets before live/dead staining.

FIG. 6 panel (c) is a fluorescent image of cells subject to 12 hours of flow of DMEM at a flow rate of 0.1 µl/min.

FIG. 6 panel (d) is a fluorescent image of cells subject to 12 hours of flow of DMEM at a flow rate of 0.2 µl/min.

FIG. 6 panel (e) is a zoomed view of a fluorescent image of dead cells of the last column of FIG. 6 panel (c).

FIG. 6 panel (f) is a zoomed in view of a fluorescent image of dead cells of chambers #3, #7, #12, and #18 of FIG. 6 panel (c).

FIG. 6 panel (g) is a cell viability chart for the last column of the chambers of different conditions.

FIG. 6 panel (h) is a chemical gradient and shear stress diagram across chambers.

FIG. 6 panel (i) is a cell viability chart from the chamber #3, #7, #12 and #18 of FIG. 6 panel (c).

FIG. 7 panel (b) are fluorescent images of a multi-well Dox study on A431 cells with different concentrations of the Dox.

FIG. 7 panel (c) is a cell viability chart comparing the DMEM/Dox condition and the multi-well study with the same concentrations.

DETAILED DESCRIPTION OF THE PRESENT DISCLOSURE

Figure 1:
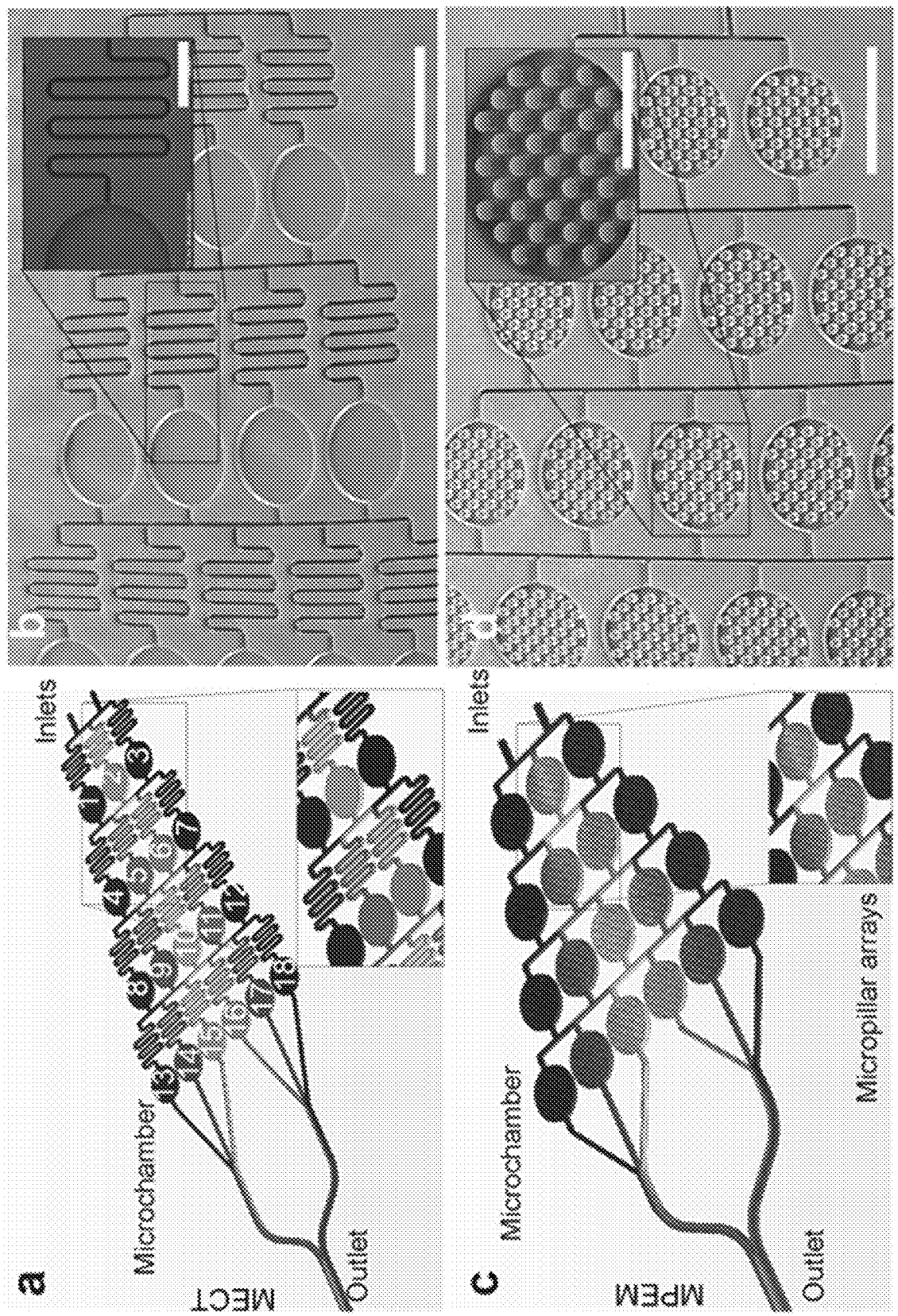
FIG. 1 panel (a) is a COMSOL simulation design of a microchamber embedded microfluidic device for gradient generation and drug screening that includes microchambers that are placed after serpentine microchannels, the configuration referred to as Microchamber-Embedded Christmas Tree (MECT).

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Before any embodiments of the invention are explained in detail, it is to be understood that the invention is not limited in its application to the details of construction and the arrangement of components set forth in the following description or illustrated in the attached drawings. The invention is capable of other embodiments and of being practiced or of being carried out in various ways. Also, it is to be understood that the phraseology and terminology used herein is for the purpose of description and should not be regarded as limiting. For example, the use of "including," "comprising," or "having" and variations thereof herein is meant to encompass the items listed thereafter and equivalents thereof as well as additional items.

As used herein, unless otherwise specified or limited, the terms "mounted," "connected," "supported," and "coupled" and variations thereof are used broadly and encompass both direct and indirect mountings, connections, supports, and couplings. Further, unless otherwise specified or limited, "connected" and "coupled" are not restricted to physical or mechanical connections or couplings.

Microchamber Embedded Gradient Generation Device Design

Mixing solutions and generating chemical gradients is an important area that has triggered numerous research activities. The most common method for generating chemical gradients in microfluidics is by mixing inlet streams containing controlled concentrations of chemicals in microchannels, and one of the common approaches arranges the microchannels in a serpentine shape. By varying the concentrations and flow rates of each microchannel inlet, these so-called "Christmas tree-like" microfluidic networks can generate a profile of chemical gradient at the outlet region. This outlet region is normally populated with different types of cells to receive the chemical gradients and to observe the responses. Nevertheless, this platform has only one culture compartment that can be used to investigate the response of the cultures to chemical gradients. Further, microfluidic devices have been extensively used as high throughput systems in a way that cellular responses to several conditions can be tested on a single chip. However, these high throughput systems cannot produce different conditions automatically and rely on a secondary system for the preparation of the culturing environment.

Considering that microfluidic channels and chambers can also facilitate cell culture and growth, an innovative design that integrates the chemical gradient generation and cell culture in one platform is described herein. To this end, in some embodiments microchambers for seeding cells and for drug testing on cultured cells were designed and placed after each serpentine channel of the Christmas tree-like design. In other embodiments, micropillars are also built into chambers to produce gradients within chambers. This integration of microchambers enables the screening of chemical gradients in individual, controlled chambers, and thus provides embodiments of apparatus, systems, and methods for high throughput screening of chemical compounds. In addition, some embodiments also allow for the co-culture of different cell types at controlled ratios.

Thus, various embodiments disclosed herein provide an apparatus, method, or system for a microfluidic device with embedded cell culture chambers for high throughput biological assays. In one embodiment, a microfluidic gradient generator apparatus may include a substrate including a plurality of microchannels and a plurality of microchambers formed therein. As described herein, the substrate may be fabricated using known procedures and may be a chip made from a material such as PDMS, although in various embodiments other materials may be used instead of or in addition to PDMS.

In some embodiments, each of the plurality of microchambers may include a first end and a second end and configured to permit fluid to flow from the first end to the second end as shown for example in FIGS. 1 and 2. In various embodiments, at least one of the first end or the second end of each of the plurality of microchambers may be coupled to at least one of the plurality of microchannels, where each of the plurality of microchannels and each of the plurality of microchambers may be fluidly coupled to an inlet and an outlet such that fluid containing a material that is introduced at the inlet flows through at least one of the plurality of microchannels and at least one of the plurality of microchambers to the outlet. In certain embodiments, the plurality of microchannels and the plurality of microchambers on the substrate may be configured so as to form a gradient of the material within the fluid.

In some embodiments, each of the plurality of microchambers may be configured for cell culture, for example 3D cell culture. In one embodiment, a microchamber may be configured for 3D cell culture by introducing a plurality of cells along with a hydrogel substance (e.g. GelMA, see below) which may be cured (e.g. through photocrosslinking) in order to support the cells in a three-dimensional culture environment.

In some embodiments, the inlet may include a plurality of inlets a first fluid including a first material may be introduced at a first flow rate into a first inlet of the plurality of inlets and a second fluid including a second material may be introduced at a second flow rate into a second inlet of the plurality of inlets, where the gradient may include a first gradient of the first material and a second gradient of the second material. In certain embodiments the first flow rate may be different from the second flow rate.

In various embodiments, at least one microchannel of the plurality of microchannels may include a serpentine microchannel (e.g. as shown in FIGS. 1 and 2), and the serpentine microchannel may be coupled to the first end of one of the plurality of microchambers. The serpentine microchannels may include multiple straight segments connected by sharp turns, e.g. as shown in FIG. 1a, which help to regulate fluid flow; although examples shown herein include five complete segments and two half segments connected by a total of six turns, serpentine microchannels having greater or fewer numbers of segments and turns are also possible. In some embodiments, at least one microchamber of the plurality of microchambers may include a plurality of micropillars therein (e.g. as shown in FIGS. 1 and 2), such that the gradient may include a gradient of the material within the at least one microchamber which includes the plurality of micropillars. In various embodiments, the number, size, and density of micropillars may be increased or decreased relative to the micropillars disclosed herein.

In various embodiments, the plurality of microchambers may be arranged on the substrate in a plurality of rows between the inlet and the outlet, where each row of the plurality of rows may include a subset of the plurality of microchambers. In particular embodiments, a number of the microchambers in each of the plurality of rows may increase from the inlet to the outlet. For example, as shown in FIG. 1a, the first such row closest to the inlet includes three microchambers, the second row includes four microchambers, the third row includes five microchambers, and the fourth row includes six microchambers.

In some embodiments, the plurality of microchannels may include a manifold, as shown in FIGS. 1 and 2. For example, as seen in FIG. 1c the manifold includes the microchannel which runs parallel to and between the third row and the fourth row, where the manifold is connected to the outlets of the microchambers in the third row and to the inlets of the fourth row. More generally, in certain embodiments the outlet of each of the plurality of microchambers in a first row of the plurality of rows is fluidly coupled to the manifold and the inlet of each of the plurality of microchambers in a second row of the plurality of rows adjacent to the first row is fluidly coupled to the manifold. In particular embodiments, each microchamber of the subset of microchambers within a row includes a different concentration of the material within the fluid.

Various embodiments provide a method for generating a microfluidic gradient. The method may include providing a substrate including a plurality of microchannels and a plurality of microchambers formed therein. As noted above and described in detail below, the substrate may be a chip made of PDMS or other suitable material. In some embodiments, each of the plurality of microchambers may include a first end and a second end and may be configured to permit fluid to flow from the first end to the second end, where at least one of the first end or the second end of each of the plurality of microchambers may be coupled to at least one of the plurality of microchannels. Further, each of the plurality of microchannels and each of the plurality of microchambers may be fluidly coupled to an inlet and an outlet. In various embodiments, the method may further include introducing a fluid containing a material at the inlet such that the fluid flows through at least one of the plurality of microchannels and at least one of the plurality of microchambers to the outlet. In some embodiments, the method may include forming a gradient of the material within the fluid within the plurality of microchannels and the plurality of microchambers on the substrate. That is, there may be a gradient within a single microchannel, as shown in FIG. 1c, and/or there may be a gradient (i.e. a difference in concentrations) of the material between two adjacent microchannels, as shown in FIG. 1a.

In some embodiments, providing a substrate including a plurality of microchannels and a plurality of microchambers formed therein may include providing the substrate in which each of the plurality of microchambers is configured for cell culture and seeding at least one microchamber of the plurality of microchambers with a plurality of cells. In various embodiments, seeding at least one microchamber of the plurality of microchambers with a plurality of cells may further include seeding the least one microchamber of the plurality of microchambers with the plurality of cells in combination with a hydrogel material to perform 3D cell culture. As noted above and described in more detail below, a microchamber may be configured for 3D cell culture by introducing a plurality of cells along with a hydrogel substance (e.g. GelMA, see below) which may be cured (e.g. through photocrosslinking) in order to support the cells in a three-dimensional culture environment. In some embodiments, the plurality of cells may include at least two different cell types.

In certain embodiments, the inlet may include a plurality of inlets such that introducing a fluid containing a material at the inlet may further include introducing a first fluid including a first material at a first flow rate into a first inlet of the plurality of inlets and introducing a second fluid including a second material at a second flow rate into a second inlet of the plurality of inlets, and where forming a gradient of the material within the fluid may include forming a first gradient of the first material and a second gradient of the second material. In particular embodiments, the first flow rate may be different from the second flow rate.

In certain embodiments, a substrate a plurality of microchannels and a plurality of microchambers formed therein may be provided in which at least one microchannel of the plurality of microchannels includes a serpentine microchannel and wherein the serpentine microchannel is coupled to the first end of one of the plurality of microchambers, as shown in FIGS. 1 and 2.

In various embodiments, a substrate including a plurality of microchannels and a plurality of microchambers formed therein may be provided in which at least one microchamber of the plurality of microchambers includes a plurality of micropillars therein, such that forming a gradient may include forming the gradient of the material within the at least one microchamber which includes the plurality of micropillars.

In some embodiments, a substrate including a plurality of microchannels and a plurality of microchambers formed therein may be provide in which the plurality of microchambers are arranged on the substrate in a plurality of rows between the inlet and the outlet, each row of the plurality of rows including a subset of the plurality of microchambers and wherein a number of the microchambers in each of the plurality of rows increases from the inlet to the outlet, as shown in FIGS. 1 and 2. In particular embodiments, a substrate including a plurality of microchannels and a plurality of microchambers formed therein may be provided in which the plurality of microchannels includes a manifold in which the outlet of each of the plurality of microchambers in a first row of the plurality of rows is fluidly coupled to the manifold and the inlet of each of the plurality of microchambers in a second row of the plurality of rows adjacent to the first row is fluidly coupled to the manifold. In some embodiments, forming a gradient may include forming the gradient including a different concentration of the material within the fluid within each microchamber of the subset of microchambers within a row. In certain embodiments, introducing a fluid may include generating a shear stress within at least one of the plurality of microchambers based on the fluid flowing through the at least one of the plurality of microchambers.

FIG. 1 shows designs of microchamber-embedded microfluidic devices for gradient generation and drug screening. FIG. 1a shows a COMSOL simulation of a microchannel embedded Christmas tree (MECT) design in which microchambers are embedded after each serpentine microchannel, where fluid flows from the inlets in the upper right corner to the outlet in the lower left corner. A gradient is generated across chambers and a uniform concentration is achieved within each chamber. The chambers are numbered (#'s 1-18 in FIG. 1a) based on their position as indicated on each microchamber. FIG. 1b shows scanning electron microscopy (SEM) images of the entire chip with insets showing a close-up view of a serpentine channel and a portion of a microchamber. FIG. 1c shows a COMSOL simulation of a micropillar embedded microchamber (MPEM) design. An overall gradient across chambers as well as a local gradient within each chamber are generated. FIG. 1d shows SEM images of the entire chip with inset showing the chamber and the micropillars. Scale bars for FIG. 1 are as follows: FIG. 1b, 1000 µm, inset, 500 µm; FIG. 1d, 1000 µm, inset, 500 µm.

FIGS. 1a and 1b show the integrated platform with the microchambers placed after the serpentine microchannels, referred to as Microchamber-Embedded Christmas Tree (MECT). As illustrated in FIG. 1a, each microchamber has different chemical concentrations with combination of two different media solutions at the two inlets; in the meantime, the concentrations within each microchamber are uniform. To produce a gradient within a microchamber, micropillars are built within each chamber to create the mixing effect and the non-uniform chemical concentration, as illustrated in FIG. 1c.

In one embodiment of so-called MicroPillar Embedded Microchambers (MPEM), the micropillar arrays form a network of flow resistors to generate gradients. The microchambers for both devices are designed to be approximately 1 millimeter in diameter to accommodate about 1,000 cells, although larger or smaller dimensions are also possible. These dimensions are also tailored to generate shear stresses in the order of $10^{-2}$ Pa at the bottom of the chamber as a mechanical stimulus for live cells (to be discussed in the following sections). FIGS. 1b and 1d show the SEM images of the PDMS chips fabricated by soft lithography for the MECT and the MPEM designs, respectively. In addition, the inset for FIG. 1b shows the dimension of the serpentine channel and the inset of FIG. 1d shows the dimension of the micropillar array (with a diameter of approximately 80 µm for each pillar).

Gradient Generation with Embedded Microchambers

Figure 2A:
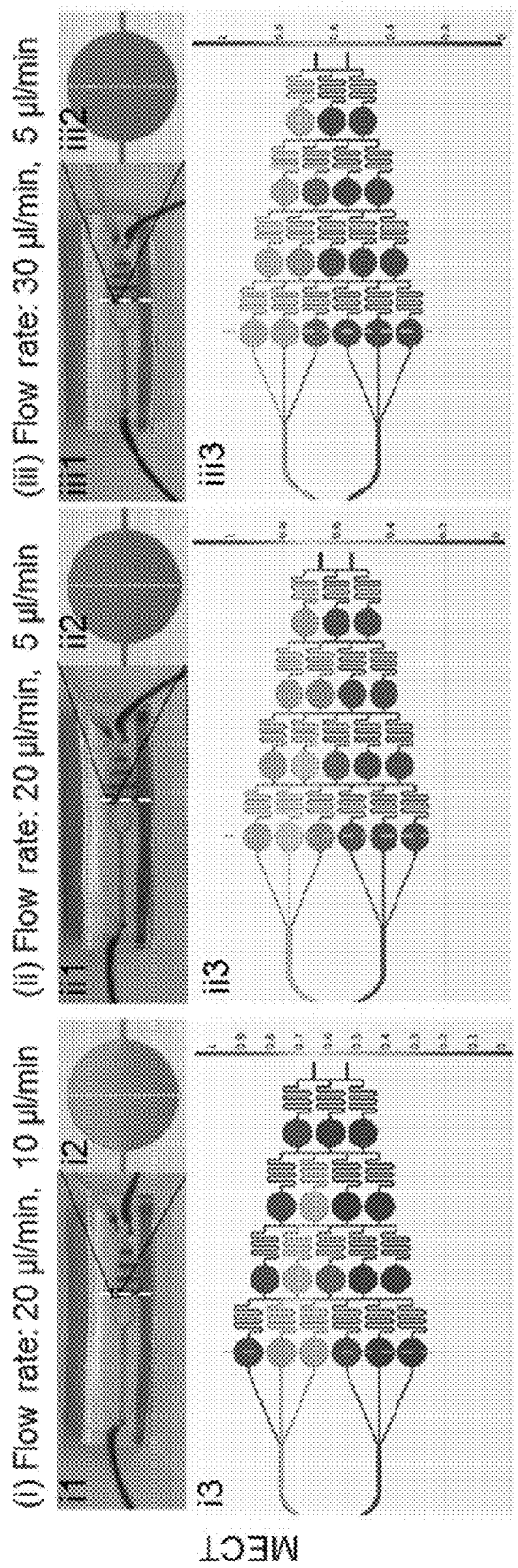
FIG. 2a shows COMSOL simulations and tests of an MECT device generating gradients with different ratios of flow rates at inlets.
Figure 2B:
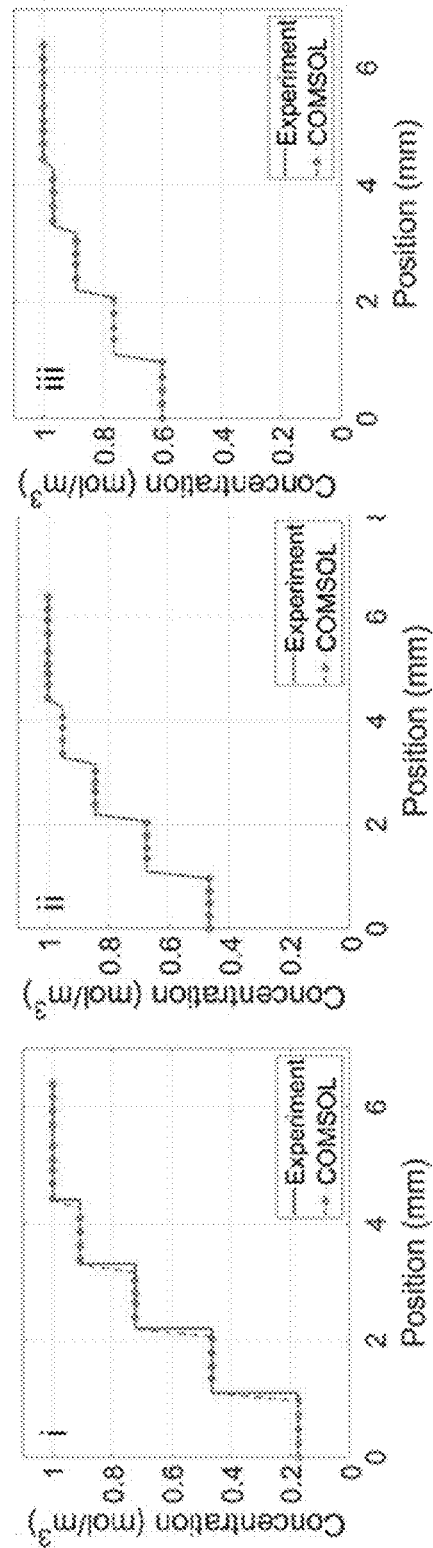
Figure 2C:
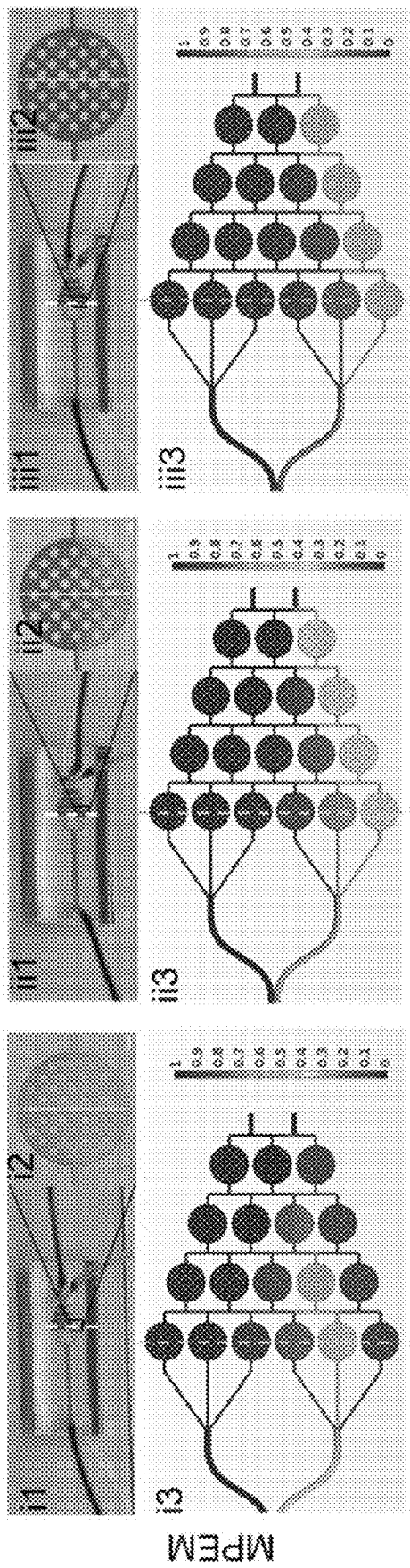
FIG. 2c shows COMSOL simulations and tests of an MPEM device generating gradients with different ratios of flow rates at inlets.
Figure 2D:
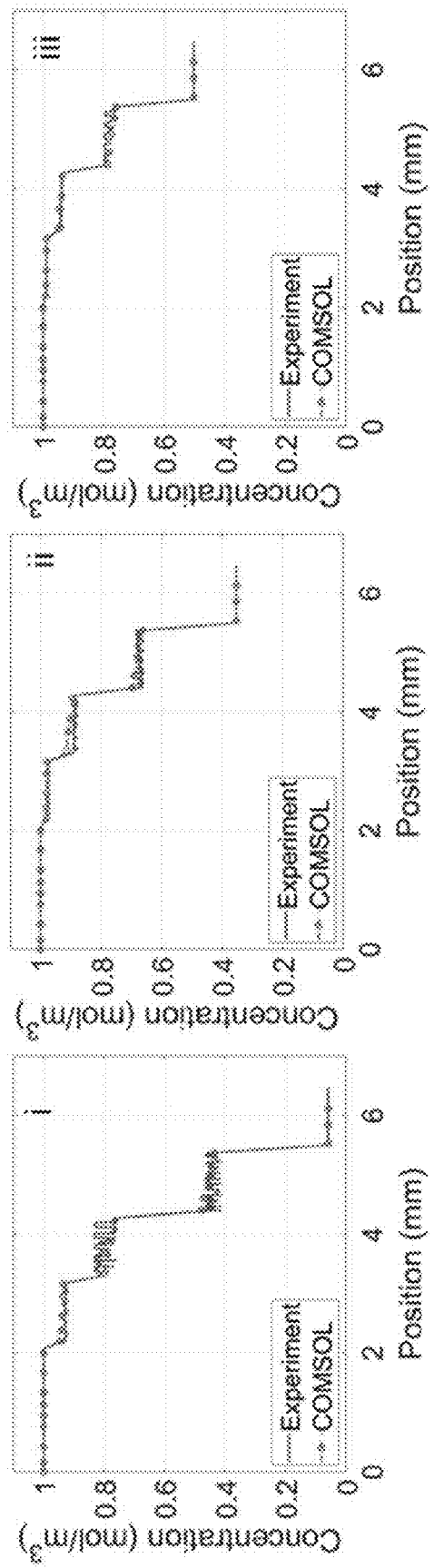
FIG. 2d shows graphical comparisons of experimental data and simulation data of the simulations and tests of FIG. 2c.

The capability of the microchamber integrated microfluidic devices in generating tunable chemical gradients across chambers and within chambers in MECT and MPEM designs, respectively, is discussed below. FIG. 2 shows gradient generation using the MECT and MPEM microfluidic channels. FIG. 2a shows testing and modeling of the MECT device in generating gradients with different ratios of flow rates at the inlets. The inlets were perfused with media of two different colors, yellow and blue. Three different velocity ratios were shown: 20/10 µl/min (shown in column i), 20/5 µl/min (shown in column ii), 30/5 µl/min (shown in column iii). For each flow rate, the device with the gradient is shown in (1), a zoom-in image of a representative chamber (#14) is shown in (2) and the COMSOL simulation is shown in (3). It is evident that variation in flow rate ratios modifies the chemical gradient produced. FIG. 2b shows a comparison of the experimental data and the simulation data for gradient generation is shown at three flow rate combinations in (i) (ii) and (iii). The gradient is captured with the RGB coloration of each chamber. The plot shows the Blue color index for center line of the last column of the device (chambers 13 through 18) normalized within 0 and 1. FIG. 2c is similar to FIG. 2a, where the experiments and simulation were conducted for the MPEM device at three different flow rate combinations: i, ii, iii. FIG. 2d shows a comparison of the MPEM device in gradient generation from the experiments and the simulation is shown. Gradients were produced across chambers and within chambers. Scale bars: 500 µm.

The capabilities of the microchamber integrated microfluidic devices can be demonstrated both experimentally and computationally with three different flow rate combinations at the two inlets from top to bottom: 20 µl/min and 10 µl/min (column (i)), 20 µl/min and 5 µl/min (column (ii)), and 30 µl/min and 5 µl/min (column (iii)). For the MECT design shown in FIG. 2a (i1, i2, ii1, ii2, iii1, iii2), experimentally, solutions with two different colors, yellow and blue, were flowed into the inlets at the designed flow rates above. Chemical gradients across all chambers in the four columns, denoted by difference in color balance, were evident for all three flow rate combinations. In COMSOL simulation shown in FIG. 2a (i3, ii3, iii3), one chemical solution containing 1 mol/m³ of chemical species serves as the input to one of the inlets and zero concentration was delivered the other inlet at flow rate combinations identical to those mentioned above. Gradient of concentrations were evident for the flow rate combinations. Moreover, images of the last six chambers were captured and processed to produce a blue color profile across the center line of the chamber. This color profile was normalized and plotted against the COMSOL simulation data in FIG. 2b.

An excellent agreement was observed for three flow rate combinations, and different ranges of chemical concentration can be realized with the three flow rate combinations (0.2 to 1 mol/m³ in FIG. 2b(i), 0.5 to 1 mol/m³ in FIG. 2b(ii), 0.6 to 1 mol/m³ in FIG. 2b(iii)). For the MPEM design shown in FIG. 2c, with the same experimental process, the chemical gradient can be produced across different chambers as well as within the individual chambers. These results also agree with the COMSOL simulation data for all flow rate combinations with the blue color from experiments plotted against the concentrations from the simulation for the last six chambers. Specifically, the chemical gradient within each chamber is in a narrower range as compared to the gradients across different chambers. The zoom-in images for the last chamber was shown in FIGS. 2a and 2c. It is worth mentioning that both devices were designed to be symmetric and were demonstrated as such.

3D Cell Seeding and Cell Culture within Embedded Chamber

FIG. 3 shows gradients of different cells encapsulated within hydrogels within the MECT microfluidic device. FIG. 3a shows a schematic illustration of the experimental process. FIG. 3b shows a fluorescent image of the gradient of stained cells with two different colors, Hoechst and green cell tracker. FIGS. 3c and 3d show zoomed-in images from representative chambers #10 and #11, respectively. FIGS. 3e and 3f show cell ratio analysis in the third and fourth columns of the chambers of the microfluidic device, respectively. Scale bars: FIG. 3b, 1000 µm; FIGS. 3c and 3d, 100 µm.

The unique capability of the microchamber-based device in 3D cell culture is discussed below. In drug screening, current microfluidic devices allow only one controlled area for cell seeding and interaction with the chemicals. The goal was to introduce spaces within the channels which serve as reaction chambers, and cells seeded within each chamber receive different dosages of the chemicals, paving the way for high throughput drug screening. Furthermore, this design provides a means to seed different cell types for co-culture, affording new potentials of screening cell-cell interactions.

Figure 3A:
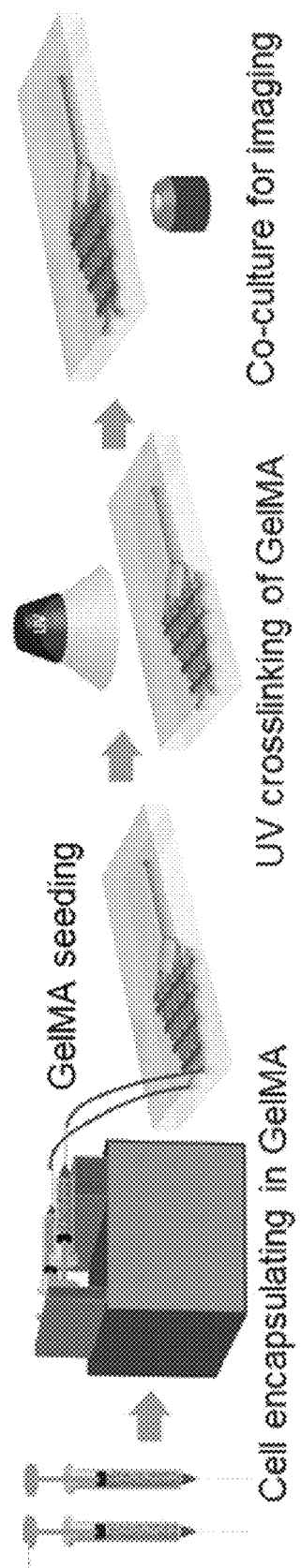
FIG. 3a is schematic illustrations of an experimental process of providing a gradient of different cells encapsulated within hydrogels within an MECT device.
Figure 3B:
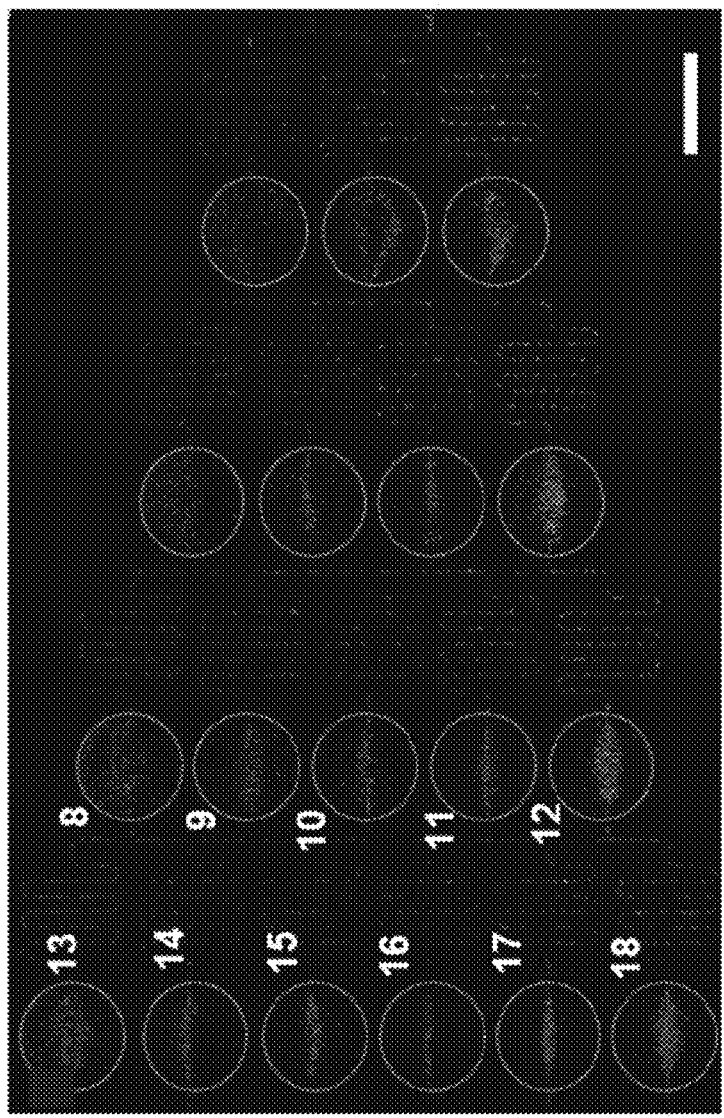
FIG. 3b is a fluorescent image of the gradient of FIG. 3a through chambers.
Figures 3C, 3D:
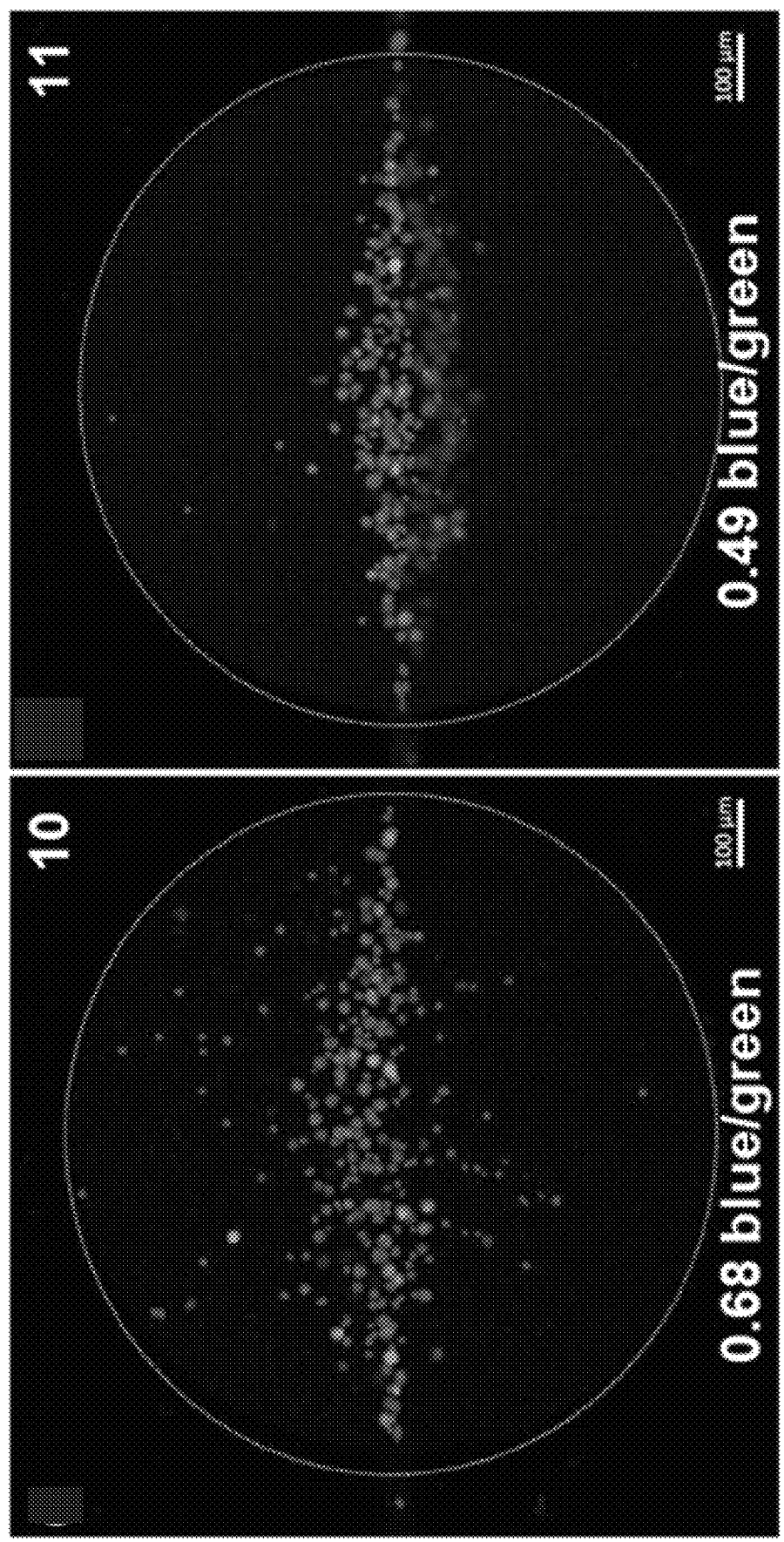
FIG. 3c is a zoomed in fluorescent image of chamber #10 of FIG. 3b.
FIG. 3d is a zoomed in fluorescent image of chamber #11 of FIG. 3b.
Figure 3F:
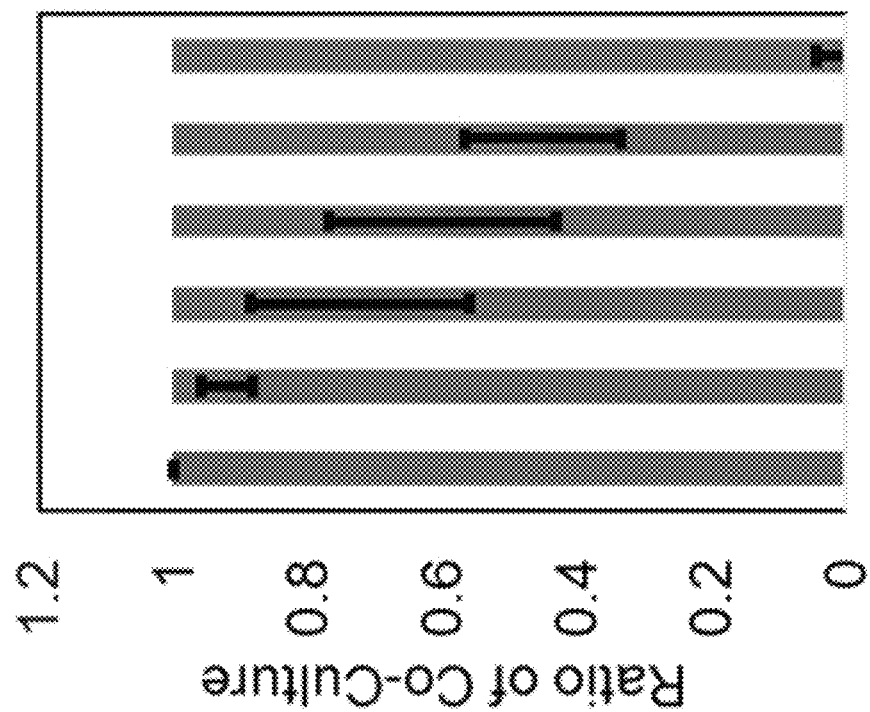
FIG. 3f is a graphical cell ratio analysis of the fourth column of the chambers of FIG. 3b.
Figure 3E:
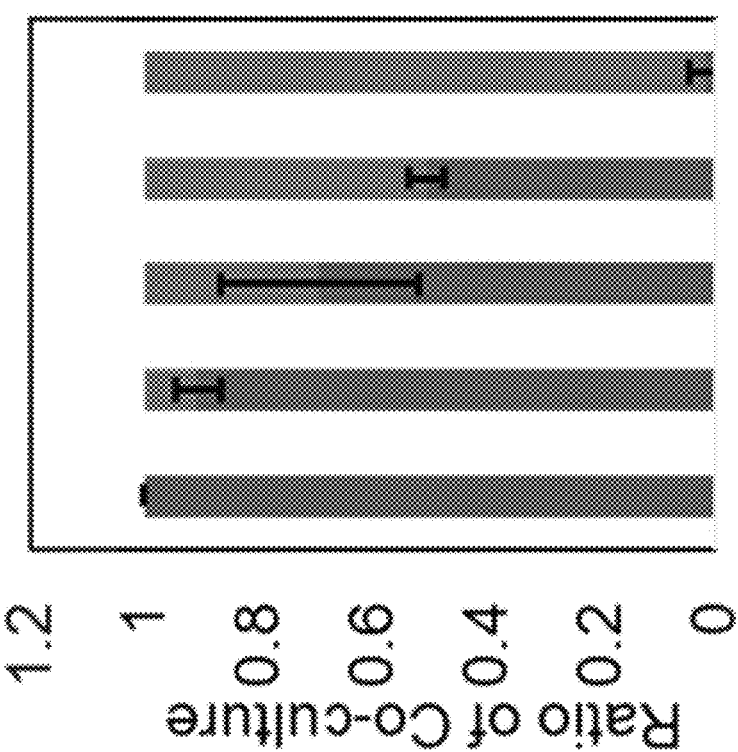
FIG. 3e is a graphical cell ratio analysis of the third column of the chambers of FIG. 3b.

To this end, two type of cells were encapsulated in 7% (w/v) gelatin methacryloyl (GelMA) solution containing photo initiators (PI) that could be cross-linked in situ to provide a 3D micro-environment. The GelMA solution was then flowed into the inlets of the MECT and MPEM devices at controlled flow rates. Once steady flow conditions were achieved, the solution flow was stopped, and a UV light was applied onto the microchambers through a mask to crosslink GelMA. The cross-linked GelMA served to encapsulate cells in a 3D environment within each microchamber. This process is illustrated in FIG. 3a. As shown in FIG. 3b, two different groups of cells (both A431 cells with different mutations) marked by two different colors were grown in the microchambers. Each chamber can produce a designated ratio of two cell types. The number of each cell type was counted, and ratios were calculated for representative chambers of #10 and #11, 0.68 and 0.49 (blue/green), respectively (FIGS. 3c and 3d). The effect of gradient can also be replicated with cell seeding in a similar fashion as in chemical gradient. The ratios of two cells in the co-culture for each chamber in the last two columns are shown in FIGS. 3e and 3f with a clearly decreasing trend of the number of blue cells for each column. In one embodiment, since the experiment was carried out at the same controlled flow rate for both inlets (30 µl/min), the cell ratio showed a symmetric pattern. It is worth mentioning that the cells were not uniformly distributed within individual chambers due to the nature of the device design. Instead, the majority of the cells were located in the centerline of the microchamber (see FIGS. 3c and 3d).

FIG. 4 shows a gradient of 3D-cell encapsulation in hydrogel within the MPEM microfluidic device embedded with a micropillar gradient generator. FIG. 4a shows a fluorescent image of the gradient of stained cells with 2 different colors, namely Hoechst and green cell tracker. FIG. 4b shows a zoomed-in image from representative chambers #10 and #11, respectively. FIGS. 4d and 4e show a cell ratio analysis in the third and fourth column of the chambers of the microfluidic device, respectively. Scale bars: FIG. 4a, 1000 µm; FIGS. 4b and 4c, 100 µm.

Figure 4A:
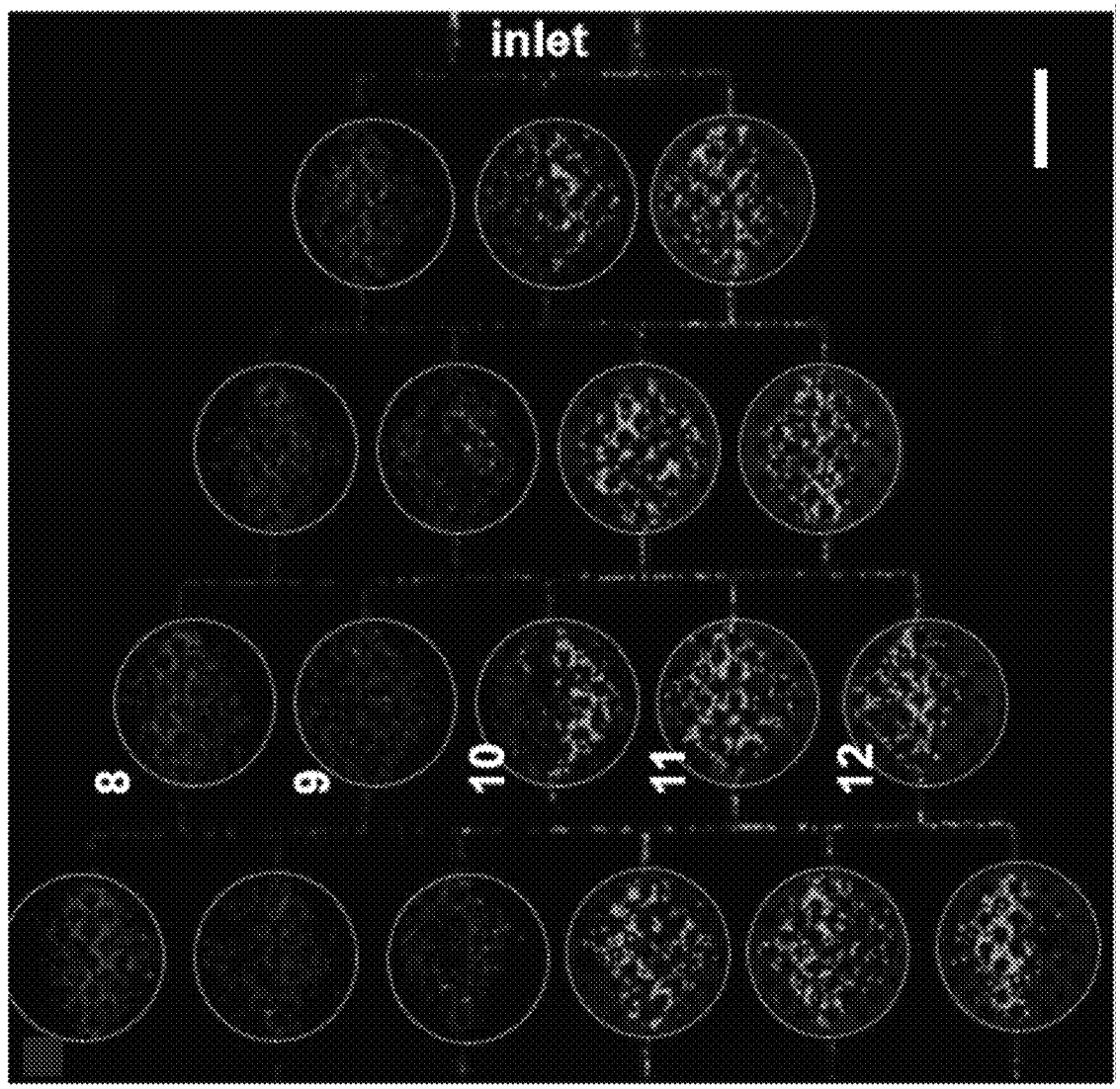
FIG. 4a is a fluorescent image of a gradient of stained cells though chambers in an MPEM device provided by cells encapsulated within hydrogel.
Figure 4C:
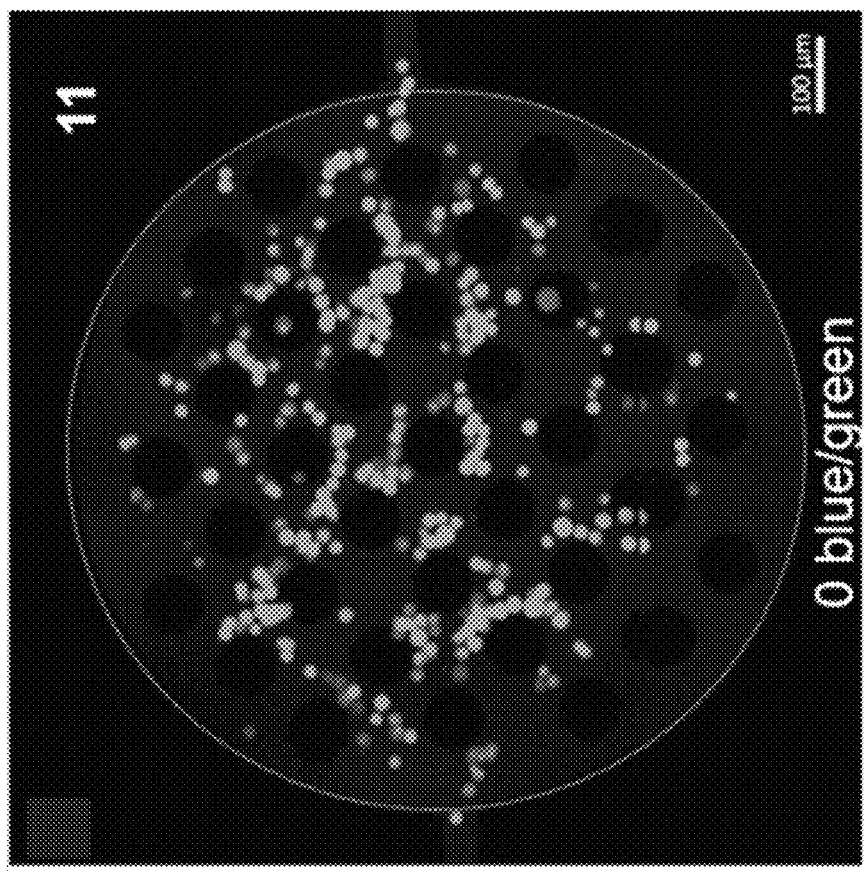
Figure 4B:
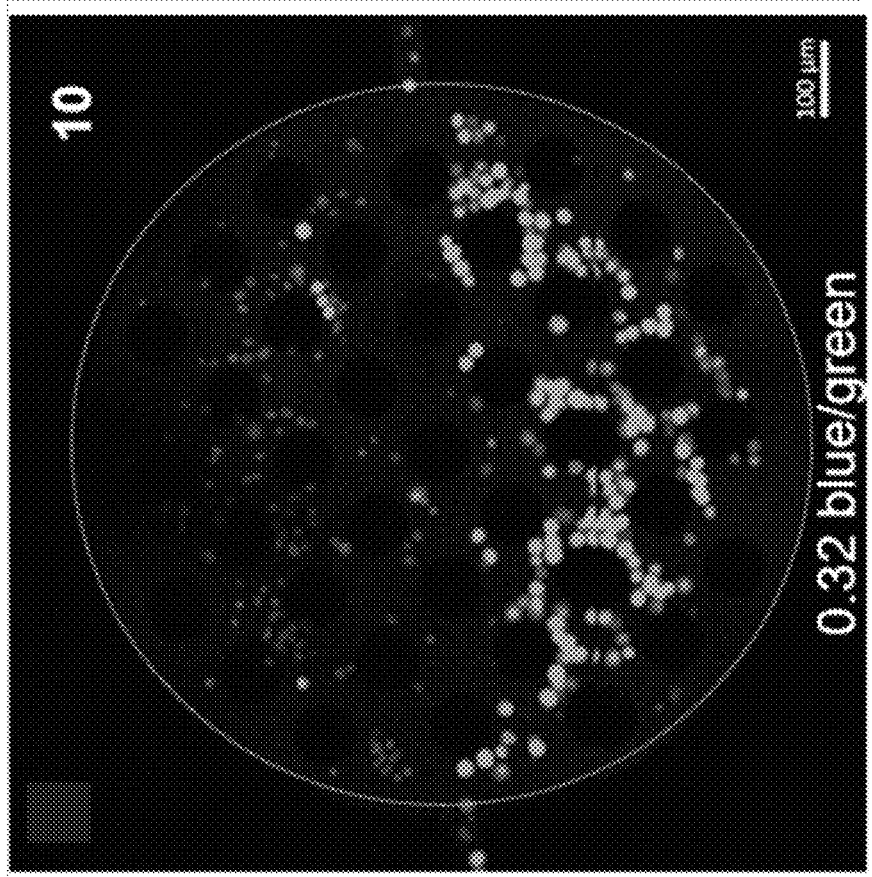
Figure 4E:
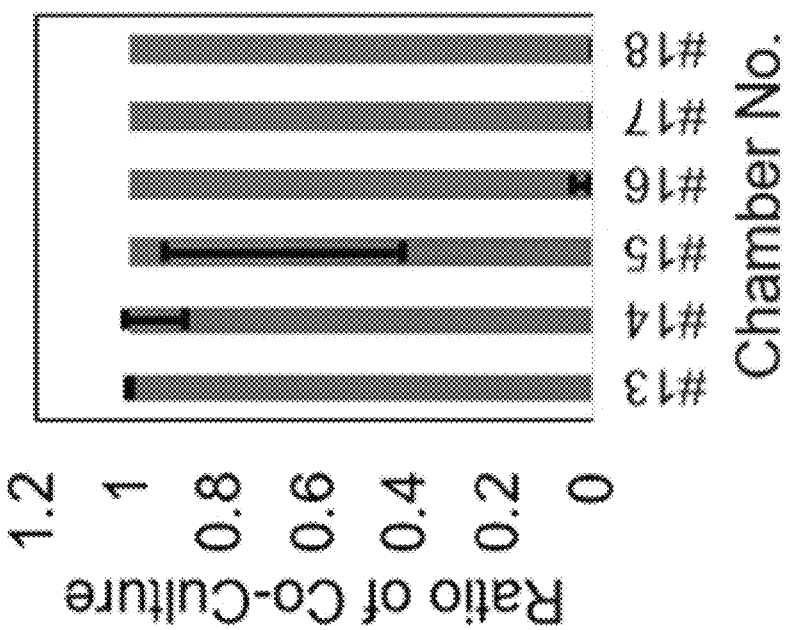
Figure 4D:
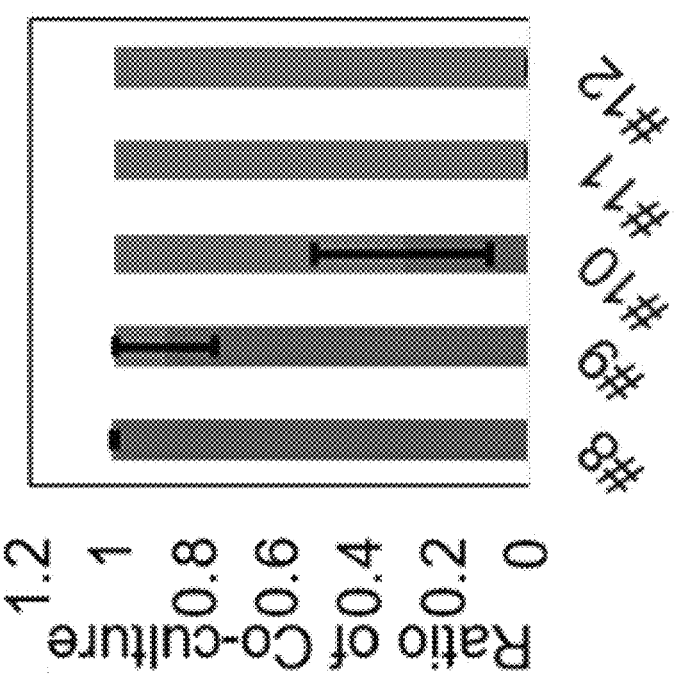

To achieve a uniform cell distribution, a similar experiment was run for the MPEM device where the micropillars induced flow alters the cell distribution, according to one embodiment. FIG. 4a shows the 3D cell encapsulation of two types of cells colored with blue and green inside the microfluidic device, and a clear gradient of cell ratios can be discerned across chambers in the same column. Similarly, since the flow rate of the cell mixture from both inlets were the same, microchambers had a symmetric distribution of both colors of cells across the center line. As the zoomed-in images of FIGS. 4b and 4c show, the distribution of the cells within chambers became more uniform as compared with FIGS. 3c and 3d, a proof that the micropillars spread the cells evenly within chambers. A clear division of two cell types was visualized from the zoom-in images, as the majority of the cells in green were seeded in the bottom half of the chamber #10 (FIG. 4b). A quantitative evaluation of the cell ratios for the last two columns of the device also provided a clear evidence of the gradient effect as the ratio of blue/green cells drops from 1 to 0 (FIGS. 4d and 4e).

This study generally provides a potential support for co-culture systems supplied with chemical gradient. In this capacity, cells can be encapsulated in 3D microenvironments with hydrogels and flowed into the microchambers with gradient effect. Once cross-linked within the microchambers, co-cultures of different cell types and ratios can be used in a wide spectrum of drug screening and immunoscreening studies. Microfluidics based co-culture systems have been studied in different cell types, including epithelial and stromal cells for mimicking prostate cancer behavior, breast cancer cells with lung cells, as well as intestine and liver cells. The majority of these studies were focused on 2D co-culture of cells, introduction of 3D co-culture with the microchamber system can create a microenvironment that is more physiologically relevant. In addition, the microchambers with the 3D co-culture can be peeled off from the top PDMS layer after cell seeding and gel crosslinking. This creates open microchambers where various biological assays can be performed on the co-culture of different cell types and ratios. Furthermore, the MPEM and MECT devices could control different ratios of cell concentrations to create co-cultures of different numbers of cells.

Effect of Gradient Drug Treatment and Shear Stress within Microchambers

The dosage effect of drugs and the effect of shear stress on cells seeded within the microchambers is discussed below. A cancer cell model which is treated with a type of chemotherapy drug, doxorubicin (Dox), commonly known as a chemical agent blocking the topo isomerase 2 enzyme in cancer cells to stop cancer cell growth, was used. The difference in cell viability for different dosages of Dox across microchambers in the device was examined. This data was compared with the dosage studies conducted in petri dishes for confirmation. Considering the effect of shear stress induced upon cells from the microfluidic flow, the efficacy of Dox in combination with the shear stress was also examined.

Figure 5:
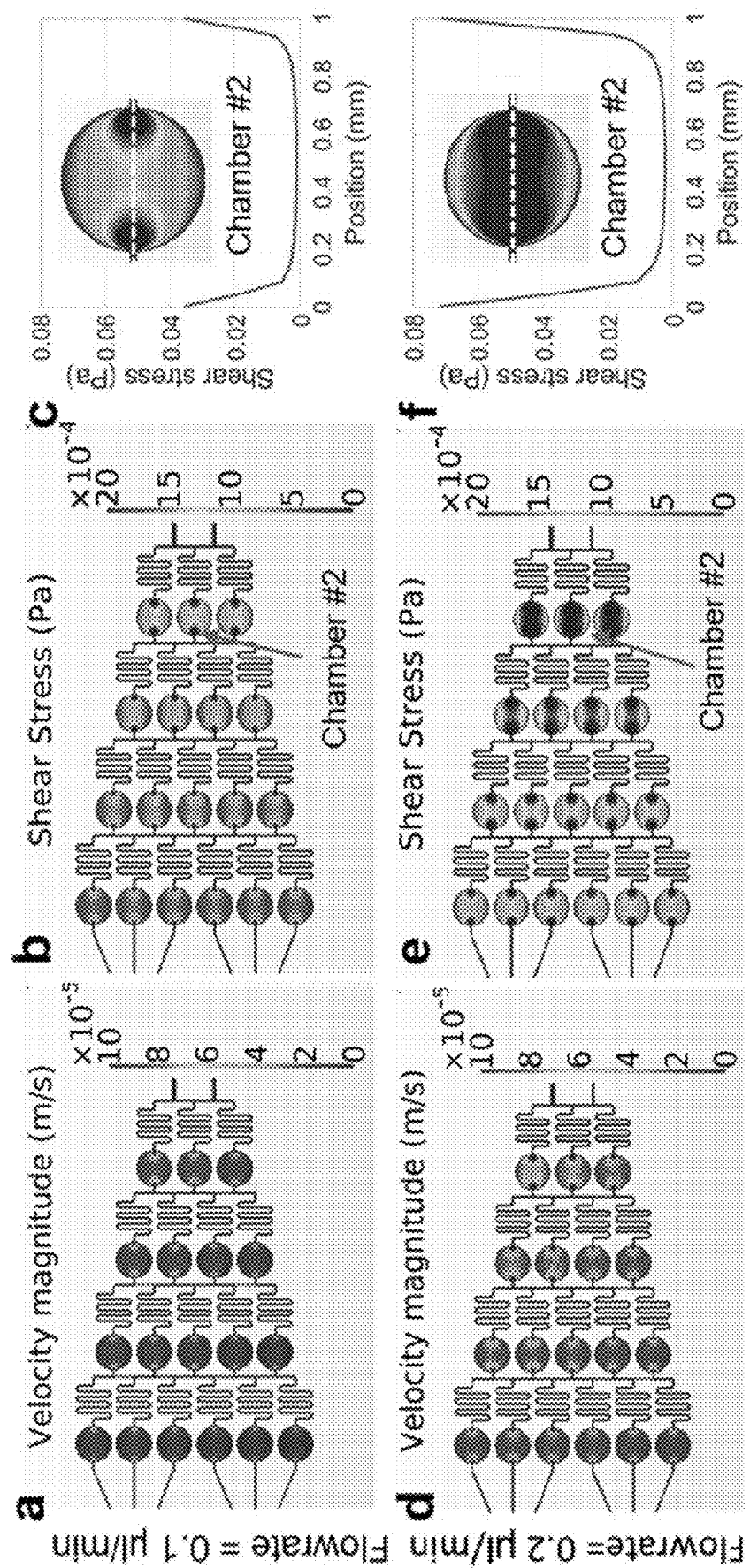
FIG. 5 panel (a) is a velocity magnitude diagram of a microchip at a flowrate of 0.1 µl/min.

FIG. 5 shows a shear stress analysis of the microchip at two flowrates. FIG. 5a shows velocity magnitude of the microchip at a 0.1 µl/min flow rate, which shows a symmetric distribution with higher magnitudes within the channels and corners compared to the chambers. FIG. 5b shows shear stress values of the microchip at a 0.1 µl/min flow rate at 15 µm distance from the surface, which shows the same trend as the velocity magnitude. The distribution of shear stress is symmetric. FIG. 5c shows shear stress distribution inside representative chamber #2 along the dashed line, which shows that the shear stress is at its maximum near the entrance and exit of the chamber and is at its minimum in the center of the chamber. FIG. 5d shows velocity magnitude for a 0.2 µl/min flow rate and also shows the same trend as the 0.1 µl/min flow rate. FIG. 5e shows a shear stress distribution for a 0.2 µl/min flow rate compared to a 0.1 µl/min flow rate, which shows higher values of shear stress with the same distribution. FIG. 5f shows shear stress values along the dashed symmetry line in chamber #2.

A COMSOL simulation of the MECT device showed that the amount of shear stress at the bottom of the microchambers, which led to morphological and physiological changes, correlates with the flow rate at the inlets of the microfluidic channel, as demonstrated by the increase of flow velocity and shear stress from a flow rate of 0.1 µl/min to 0.2 µl/min (FIGS. 5a-5f). In addition, shear stress decreased significantly from the chambers in the columns close to the inlets (#1, #2, #3) to the chambers close to the outlet (#13, #14, #15, #16, #17, #18) due to changes in the cross-sectional area and the flow rate in each column. Further, shear stress displayed a specific pattern within the chamber with the high magnitude stress closer to the inlet and outlet of the chamber, as shown by the cross-section of the shear stress distribution within chamber #2 for both flow rates (FIGS. 5c and 5f).

Figure 6:
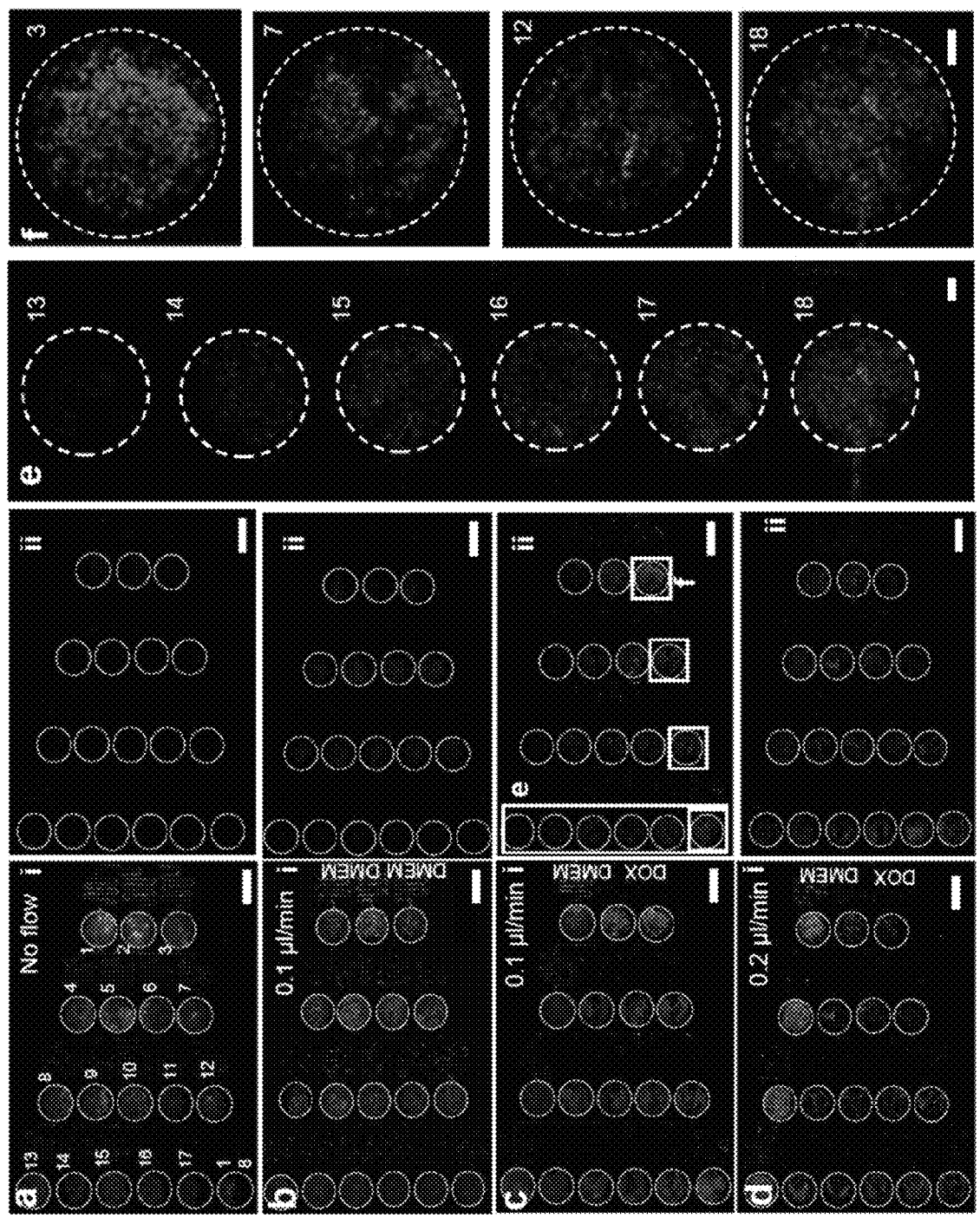
FIG. 6 panel (a) is a fluorescent image of cells stained with live/dead assay 24 hours after seeding as control.

FIG. 6 shows drug screening treatments on A431 cells using the microfluidic device. Four testing conditions were shown: FIG. 6a shows cells which were stained with a live/dead assay 24 h after seeding as a control; FIG. 6b shows cells that were subject to 12 h of flow of DMEM from both inlets before live/dead staining; FIGS. 6c and 6d shows cells that were subject to 12 h of flow of DMEM/Dox (at a concentration of 30 µg/ml) (DMEM for the top inlet, DMEM/Dox for the bottom inlet) at flow rates of 0.1 µl/min (FIG. 6c), and 0.2 µl/min (FIG. 6d) for both inlets. For each condition, composite images for live/dead cells (green and red) are shown in (i) and the dead cells (red) are shown in (ii). FIG. 6e shows zoomed-in images from the fluorescent image of the dead cells of the last column (chambers #13 through #18) for the 0.1 µl/min DMEM/Dox condition showing the increase in the number of dead cells. FIG. 6f shows zoomed-in images from chambers #3, #7, #12 and #18 for the 0.1 µl/min DMEM/Dox condition showing the increase in the number of dead cells. FIG. 6g shows cell viabilities in the last column of the chambers in the microfluidic device for: no-flow, 0.1 µl/min DMEM/DMEM, 0.05 µl/min DMEM/Dox, 0.1 µl/min DMEM/Dox and 0.2 µl/min DMEM/dox. FIG. 6h illustrates shear stress increases in columns of chambers close to the inlet, while Dox concentration increases in each column from the top chamber to the bottom chamber. FIG. 6i shows cell viability from the chamber #3, #7, #12 and #18 for the 0.1 µl/min DMEM/Dox condition. Scale bars: FIGS. 6a-6d, 1000 µm; FIG. 6e, 200 µm; FIG. 6f, 100 µm.

Taking advantage of the ability of the MECT device in generating uniform gradient within each chamber, a drug screening study with A431 cells administrated with control media and Dox was performed. Five conditions were studied: (1) Cells were stained with live/dead assay 24 hours after seeding without any media flow. This serves as the control; (2) cells were perfused by DMEM from both inlets for 12 hours before live/dead staining. This experiment examined the effect of shear stress on cell viability; (3, 4, 5) cells were perfused for 12 hours with DMEM/Dox (at a concentration of 30 µg/ml) from the bottom inlet and DMEM from the top inlet at flow rates of 0.05 µl/min (3), 0.1 µl/min (4) and 0.2 µl/min (5) for both inlets. Representative images for the studies of condition 1, 2, 4 and 5 are shown in FIGS. 6a-6d and of condition 3 in FIG. 7a. These studies were performed after the cells had been seeded within the microchambers for 24 hours. Live/dead assay staining after 2 hours of perfusion showed that cells remained attached and spread across chambers with a high viability, an average of 95% for all chambers as shown in FIG. 6a(i) (live cells in green) and FIG. 6a(ii) (dead cells in red). This provided clear evidence that cells within each chamber were viable and the device works properly. The effect of shear stress was then examined by perfusion of both inlets with a control media, Dulbecco's Modified Eagle Medium (DMEM) at a flow rate of 0.1 µl/min. Overall a slightly lower cell viability, at an average of 88%, was observed due to the shear induced cell death (FIG. 6b). In addition, the cell viability increased from the columns closest to the inlet of the device to the columns closes to the outlets, in agreement with COMSOL simulation where the shear stress is higher in the columns close to the inlets (FIG. 5).

Flowing Dox in combination with DMEM at the inlets produced the chemical gradient of Dox across chambers as expected and this concentration gradient clearly induced different cell viability across chambers. First, the higher dosage in FIG. 6d due to the higher flow rate at 0.2 µl/min reduced the overall cell viability as compared with a same dosage at lower flow rate of 0.1 µl/min in FIG. 6c. Second, this gradient induced a varied cell viability across chambers within each column for both flow rate due to the drug concentration. For both flow rate, the cell viability decreased significantly from the top chamber of each column where the Dox concentration is the lowest to the bottom chamber of each column where the Dox concentration is the highest (FIG. 6c(ii) and FIG. 6d(ii)). Representative images in FIG. 6e show a group of zoom-in images of the live/dead staining for chambers #13 through #18 in condition 4 (0.1 µl/min DMEM/Dox), clearly demonstrating the increase in the number of dead cells from #13 to #18 with the increase of Dox concentration. A quantitative data set summarizing all five conditions in FIG. 6g shows the overall decline of cell viability from chambers #13 to #18 for the three flow rates with DMEM/Dox combination (condition 3 through 5); while the cell viability remains stable for control with no flow and for DMEM only flow rate of 0.1 µl/min (both inlets) flow rate (condition 1 and 2). Some of the larger error bars in the FIG. 6g plots may be due to the difference in cell confluency before the drug test experiments due to the difference in the number of cells seeded in the chambers throughout different trials.

A synergistic effect was observed between the drug treatment and the shear stress via the overall cell viability and the patterns of cells attached within individual chambers after drug treatment. First, due to the high shear stress produced at higher flow rate in condition 5 (0.2 µl/min DMEM/Dox), the overall cell viability in condition 5 is clearly lower than that in condition 4 (0.1 µl/min DMEM/Dox), shown in images of FIG. 6c(ii) and FIG. 6d(ii) as well as the quantitative data in FIG. 6g. Significant cell detachment induced by a combined effect of shear stress and drug treatment can be observed in chambers with higher Dox concentration and with higher shear stress at the columns close to the inlet of the device, such as chambers #3, #7 in the zoom-in images of FIG. 6f. In addition, there is a clear pattern of flow-induced cell detachment, as marked in FIG. 6c(i), and the pattern shows agreement with the simulation data in FIG. 5c, where regions of higher shear stress has less cells attached and alive.

Figure 7:
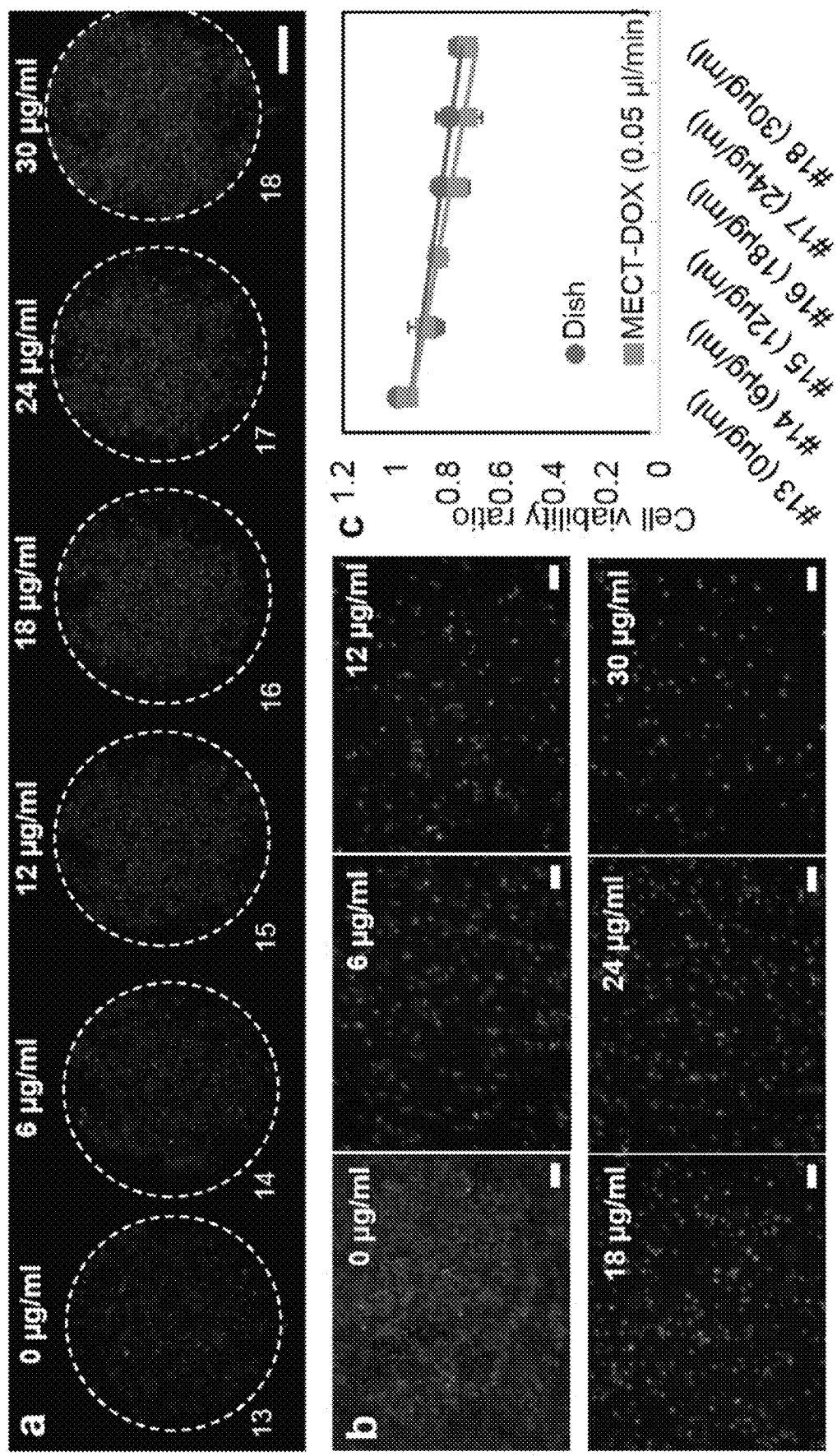
FIG. 7 panel (a) are fluorescent images of stained dead cells in a 0.05 μl/min DMEM/Dox condition.

The effect of the Dox concentration on cell viability across different chambers was confirmed by a comparative study with drug tests in a petri dish. FIG. 7 shows a comparison of the cell viability with multi-well dish study and microfluidic device study. FIG. 7a shows fluorescent images of the stained dead cells in the 0.05 µl/min DMEM/Dox condition from last column of chambers, from chambers #13 to #18, are placed left to right in this image. FIG. 7b shows fluorescent images from a multi-well Dox study on A431 cells with different concentration of the Dox. FIG. 7c shows cell viabilities within the chamber of the last column of the microfluidic device in the DMEM/Dox condition compared with cell viability of the multi-well study with the same concentrations. Scale bars: FIG. 7a, 200 µm; FIG. 7b, 100 µm.

Viability data with DMEM/Dox at the inlets at a flow rate of 0.05 µl/ml was compared with Dox treatment of A431 cells in static culture. A lower flow rate was chosen to minimize the effect of the shear stress on cell detachment and cell death. Representative images of live/dead staining after DMEM/Dox flow for the last column (chambers #13 through #18) are shown in FIG. 7a. Cell viabilities data was collected by counting cells stained green and red from these chambers. According to simulation data, the concentration of Dox in the chambers 13 through 18 are: 0 µg/ml, 6 µg/ml, 12 µg/ml, 18 µg/ml, 24 µg/ml and 30 µg/ml. These dosages were applied in static culture and the viability data were collected. Representative images of static culture treated with Dox of different concentrations are shown in FIG. 7b. The quantitative data presented in FIG. 7c for both studies showed reasonable agreement, thereby verifying the effectiveness of the device in drug screening.

The proposed chip provides a platform where not only screening of drug dosages can be performed in high throughput on small microchambers, but also the synergistic effect between mechanical stimulants and chemical compounds can be explored in dosage dependent manner. The chemical gradients, produced in chambers in the same column, and the shear stress gradient, generated due to microfluidic flow across different columns from the inlet to the outlet, create a matrix of chambers where the effect of different combinations of chemical and mechanical treatments can be examined. This concept is illustrated in FIG. 6h, where arrows points to the direction of magnitude increase in shear stress and in chemical concentrations; and anti-cancer studies clearly demonstrated that the increase in dosage and in shear stress synergistically enhanced higher cell death rate. This capability can be considered a step forward as compared with devices that only test the effect of chemical gradients on organoids and cell cultures or studies that only examine the effect of shear stress on cancer cells. It should be noted that this is a robust platform and then number of chambers can be expanded to include more concentration; while the shape of the microchamber can be modified to produce different shear stress profiles (such as in MPEM to introduce micropillars). Further, the microchambers can be tethered at the bottom onto additional PDMS layers separated by a thin porous membrane to introduce additional stimulants, such as other chemical compounds or oxygen.

Embodiments of the present disclosure include a microfluidic platform integrating chemical gradient generation and 3D cell culture in a single device. This was achieved by integrating microchambers within network of microchannels. In one design, micropillars were embedded in the chambers. The microchambers provided spaces for cell seeding and growth, and offer a reaction zone for drug screening. A process for gradient generation using the new devices and the method for 3D cell co-culturing with this platform has been shown. A gradient effect in a cancer cell model subject to a chemotherapy agent has been demonstrated. The results show the effect of Dox gradient in the induction of cell death with a clear correlation. Further, the synergistic effect of Dox concentrations in the context of fluid shear stress was observed and analyzed. Finally, these data in cell viability induced in separate chambers at different concentrations of Dox was confirmed with experiments in petri dishes with corresponding concentrations. Collectively, these data demonstrate the effectiveness of the device in potentially conducting high throughput drug screen with a single chip.

Microfluidic Device Fabrication

The fabrication process mainly consists of two steps: the design and fabrication of a silicon mold, and the fabrication of the microfluidic chip. For mold fabrication, a chromium mask coated with a thin layer of SU-8 (Kayaku Advanced Materials, MA, USA) was etched using a Laser Writer (Heidelberg DWL-66 FS, CA, USA) and an AZ-400K developer (Microchemicals GmbH, Germany) through a chemical reaction. CR-7 chromium etchant (CYANTEK Corporation, CA, USA) was subsequently used to remove the chromium layer. To ensure that no photoresist remained, a higher concentration (85% water) of AZ-400K developer was used to dissolve the remaining SU-8. To fabricate the designed features on the Si wafer, S1813 (Microposit, MA, USA) positive photoresist was selected for soft lithography. The photoresist was spin-coated on the wafer. Then, masked aligned on the top surface of the wafer and DRIE were performed to project the features on the wafer. Then, plasma etching was done to remove the photoresist. In some embodiments the chip may be made of polydimethylsiloxane (PDMS) (Sylgard 184, Corning, NY). PDMS was mixed with a curing agent in a 1:10 volume ratio and left in a desiccator for 30 min to de-gas. The wafer was washed with 99% isopropanol and dried using nitrogen gas. To avoid PDMS adhesion to the wafer, Trichloro (1H,1H,2H,2H-perfluorooctyle, Silane 97%) (Sigma Aldrich, St. Louis, MO) was used as the silane agent. The degassed PDMS was poured over the entire mold and it was again placed inside a desiccator for 30 min to remove any air bubbles formed during pouring. Finally, the wafer was thermally cured inside an oven at 65° C. for 2 hours.

Scanning Electron Microscopy (SEM)

The PDMS microfluidic chip without the glass slide was used for SEM imaging. A thermal treatment was applied to the chip in the oven at 50° C. for 30 minutes before coating to remove excessive humidity and enhance the coating process. Then chromium sputter coater (Denton Desk V Sputter) was used to coat a thin layer of chromium on the chip for 15 minutes. The coated chip was fixed to an SEM holder and then inserted into the SEM (Hitachi S4700 FE). Low magnification mode with 15 kV was used to image the whole chip for the pillar design and serpentine design with 20× and 25× magnification, respectively. High magnification mode with 15 kV was used to image one chamber for the MPEM and MECT with 130× and 67×, respectively.

COMSOL Simulation

To evaluate the performance of the microchip, a computational fluids dynamics (CFD) simulation was developed using COMSOL Multiphysics. "Creep flow" and "Transport of Diluted Species" physics were used to model the fluid flow, shear stress, and concentration changes in the microfluidic device. For the gradient studies, the inlets have different flow rates to show the effect of flow rate and their ratios on the generated gradient. However, for the shear stress study, both inlets have the same flow rates to study the effect of mechanical stimulation on the cell viability. Two flow rates were examined to investigate the effect of flow rate on the shear stress. Shear stress was calculated by adding the following equation to COMSOL analysis: $\tau=\dot{\gamma}\times\mu$, where τ is the shear stress, γ̇ is the shear rate and μ is solution viscosity. Shear rate is calculated by the software and viscosity is the fluid property. Water was the assumed fluid.

Cell Culture

A431 cell and A431 cells with GFP tagged E-cadherin (r) are cultured in T75 flasks with DMEM included 10% fetal bovine serum (FBS) and 1% penicillin-streptomycin (10,000 Unit/mL) for two days until cells reach confluency. Before the experiment, media was removed, and the flask was washed with PBS for two times. Cells were then trypsinized and suspended for use.

3D Cell Encapsulation

GelMA was used as a hydrogel to encapsulate the cells inside the chambers and two types of cells were used to demonstrate the co-culturing. GelMA was synthesized by following standard protocols. Methacrylic anhydride (MA) (Sigma Aldrich, St. Louis, MO) was mixed with liquid Gelatin in PBS with ratio of 1.25% (v/v). Subsequently, freeze-dried GelMA was dissolved in PBS and combined with solution of the Irgacure 2959 (2-Hydroxy-4'-(2-hydroxyethoxy)-2-methylpropiophenone) and PBS. The final ratio of the photo initiator (PI) was 0.1% and final ratio of the GelMA was 7%. The optimal ratio of the PI was reached by a live/dead study of the cell encapsulation within 7% GelMA crosslinked by different PI ratios.

A431-F4 and A431-I3 are the cell lines used for 3D co-culturing the cells. Cells were stained with either Horst or green cell tracker and mixed with the GelMA solution. The final concentration of cells encapsulated in GelMA solution was around 5 million cells per ml. The GelMA-cell mixture was filled into the 1 mL syringes and flowed into the microchannels with syringe pumps at controlled flow rates. Once a stable condition was reached inside the microchannels, the infusion was stopped and the GelMA was cured under the UV laser chamber with the intensity of 750 mw for 30 seconds.

Cell Seeding for Drug Study

As discussed in microchannel fabrication, PDMS with ratio 1:10 were used to fabricate the microchannel and it was bonded to glass-slides and cured for 30 min at 80° C. inside the oven. Human fibronectin protein (Thermofisher) with the concentration of 50 μg/ml was used to coat the surface of the glass-slide as the bottom layer of the microchannels. Fibronectin was flowed into the microchannels by syringes and incubated for 2 hours. The fibronectin coated microchannel was washed with PBS. A mixture of the cell and DMEM was flowed into the microchannel by syringe pump at a flow rate (30 μl/min). The concentration of cell mixture was about 10 million cells per ml of media. Cell attachment and proliferation inside the microchannel was reached by placing the microchannel inside the incubator for 24 hours.

Drug Testing and Live/Dead Assay

Doxorubicin hydrochloride 98.0-102.0% (HPLC) with molecular weight of 579.98 was dissolved in water and was diluted in DMEM media. For A431 cells, live-dead staining kit was diluted with PBS and was continuously flowed into the chambers with cells for 2 hours. Live-dead kit contains, Calcein-AM which stains green to the cytoskeleton of live cells and ethidium homodimer which stains red to the nuclei of dead cells. Cells were then counted with ImageJ cell counter module. Viability of the cells was calculated as the ratio of the live cells (stained green) over the total number of the cell, summation of the live (green) and dead (red) cells within each chamber.

Imaging

ZEISS LSM 800 confocal microscope (4×, 1.4NA) was used for live and fixed cell imaging. All images were captured with ZEN software (ZEN, 2017, Zeiss). Bright field images were taken with Nikon Ti2 using NIS-Ar software. All image reconstruction and channel alignment were performed using the ImageJ software.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A microfluidic gradient generator system, comprising:
a substrate comprising a plurality of microchannels and a plurality of microchambers formed therein, and
a plurality of fluids comprising a first fluid and a second fluid,
the substrate including a plurality of inlets and an outlet,
each of the plurality of microchambers including a first end and a second end and permitting fluid to flow from the first end to the second end,
the plurality of microchambers being arranged on the substrate in a plurality of rows between the plurality of inlets and the outlet, each row of the plurality of rows comprising a subset of the plurality of microchambers, and
a number of the microchambers in each of the plurality of rows increasing from the inlet to the outlet,
at least one of the first end or the second end of each of the plurality of microchambers being coupled to at least one of the plurality of microchannels,
each of the plurality of microchannels and each of the plurality of microchambers being fluidly coupled to the plurality of inlets and the outlet such that fluids containing materials that are introduced at the inlet flow through at least one of the plurality of microchannels and at least one of the plurality of microchambers to the outlet,
the plurality of microchannels and the plurality of microchambers on the substrate forming a gradient of the materials within the fluid,
the materials comprising a first material and a second material,
the plurality of inlets comprising a first inlet and a second inlet,
the first fluid including the first material being introduced at a first flow rate into the first inlet of the plurality of inlets,
the second fluid including the second material being introduced at a second flow rate into the second inlet of the plurality of inlets, and
the gradient comprising a first gradient of the first material and a second gradient of the second material.

2. The system of claim 1, each of the plurality of microchambers being configured for cell culture.

3. The system of claim 2, the cell culture being 3D cell culture.

4. The system of claim 1, the first flow rate being different from the second flow rate.

5. The system of claim 1, at least one microchannel of the plurality of microchannels comprising a serpentine microchannel, and
the serpentine microchannel being coupled to the first end of one of the plurality of microchambers.

6. The system of claim 1, at least one microchamber of the plurality of microchambers comprising a plurality of micropillars therein, and
the gradient comprising a gradient of the material within the at least one microchamber comprising the plurality of micropillars.

7. The system of claim 1, the plurality of microchannels comprising a manifold,
the outlet of each of the plurality of microchambers in a first row of the plurality of rows being fluidly coupled to the manifold, and
the inlet of each of the plurality of microchambers in a second row of the plurality of rows adjacent to the first row being fluidly coupled to the manifold.

8. The system of claim 1, each microchamber of the subset of microchambers within a row comprising a different concentration of the material within the fluid.

9. A method for generating a microfluidic gradient, comprising:
providing a plurality of fluids comprising a first fluid and a second fluid;
providing a substrate comprising a plurality of microchannels and a plurality of microchambers formed therein,
the substrate including a plurality of inlets and an outlet, the plurality of inlets comprising a first inlet and a second inlet,
each of the plurality of microchambers including a first end and a second end and permitting fluid to flow from the first end to the second end,
the plurality of microchambers being arranged on the substrate in a plurality of rows between the plurality of inlets and the outlet, each row of the plurality of rows comprising a subset of the plurality of microchambers, and
a number of the microchambers in each of the plurality of rows increasing from the inlet to the outlet,
at least one of the first end or the second end of each of the plurality of microchambers being coupled to at least one of the plurality of microchannels, and
each of the plurality of microchannels and each of the plurality of microchambers being fluidly coupled to the plurality of inlets and the outlet;
introducing fluids containing materials at the plurality of inlets such that the fluids flow through at least one of the plurality of microchannels and at least one of the plurality of microchambers to the outlet,
the materials comprising a first material and a second material,
introducing the fluids comprising:
introducing the first fluid including the first material at a first flow rate into the first inlet of the plurality of inlets, and
introducing the second fluid including the second material at a second flow rate into the second inlet of the plurality of inlets; and
forming a gradient of the materials within the fluids within the plurality of microchannels and the plurality of microchambers on the substrate,
the gradient comprising a first gradient of the first material and a second gradient of the second material.

10. The method of claim 9, providing a substrate comprising a plurality of microchannels and a plurality of microchambers formed therein further comprising:
providing the substrate in which each of the plurality of microchambers is configured for cell culture, and
seeding at least one microchamber of the plurality of microchambers with a plurality of cells.

11. The method of claim 10, seeding at least one microchamber of the plurality of microchambers with a plurality of cells further comprising:
seeding the least one microchamber of the plurality of microchambers with the plurality of cells in combination with a hydrogel material to perform 3D cell culture.

12. The method of claim 11, seeding the least one microchamber of the plurality of microchambers with the plurality of cells further comprising:
seeding the least one microchamber of the plurality of microchambers with the plurality of cells,
the plurality of cells comprising at least two different cell types.

13. The method of claim 9, the first flow rate being different from the second flow rate.

14. The method of claim 9, providing a substrate comprising a plurality of microchannels and a plurality of microchambers formed therein further comprising:
providing the substrate in which at least one microchannel of the plurality of microchannels comprises a serpentine microchannel and in which the serpentine microchannel is coupled to the first end of one of the plurality of microchambers.

15. The method of claim 9, providing a substrate comprising a plurality of microchannels and a plurality of microchambers formed therein further comprising:
providing the substrate in which at least one microchamber of the plurality of microchambers comprises a plurality of micropillars therein, and forming a gradient further comprising:
forming the gradient of the material within the at least one microchamber comprising the plurality of micropillars.

16. The method of claim 9, providing a substrate comprising a plurality of microchannels and a plurality of microchambers formed therein further comprising:
providing the substrate in which the plurality of microchannels comprises a manifold,
the outlet of each of the plurality of microchambers in a first row of the plurality of rows being fluidly coupled to the manifold, and
the inlet of each of the plurality of microchambers in a second row of the plurality of rows adjacent to the first row being fluidly coupled to the manifold, and forming a gradient further comprising:
forming the gradient comprising a different concentration of the material within the fluid within each microchamber of the subset of microchambers within a row.

17. The method of claim 9, introducing a fluid further comprising:
generating a shear stress within at least one of the plurality of microchambers based on the fluid flowing through the at least one of the plurality of microchambers.

* * * * *